(12) United States Patent
Wittwer et al.

(10) Patent No.: US 7,297,484 B2
(45) Date of Patent: Nov. 20, 2007

(54) CHARACTERIZATION OF SINGLE STRANDED NUCLEIC ACIDS BY MELTING ANALYSIS OF SECONDARY STRUCTURE USING DOUBLE STRAND-SPECIFIC NUCLEIC ACID DYE

(75) Inventors: Carl T. Wittwer, Salt Lake City, UT (US); C. Wade Dummer, Layton, UT (US)

(73) Assignees: Idaho Technology, Salt Lake City, UT (US); University of Utah Research Foundation, Salt Lake City, UT (US)

( * ) Notice: Subject to any disclaimer, the term of this patent is extended or adjusted under 35 U.S.C. 154(b) by 410 days.

(21) Appl. No.: 10/423,621

(22) Filed: Apr. 25, 2003

(65) Prior Publication Data

US 2004/0033518 A1 Feb. 19, 2004

Related U.S. Application Data

(60) Provisional application No. 60/375,640, filed on Apr. 26, 2002.

(51) Int. Cl.
*C12Q 1/68* (2006.01)
*C07H 21/02* (2006.01)
*C07H 21/04* (2006.01)

(52) U.S. Cl. .................. 435/6; 536/23.1; 536/24.3
(58) Field of Classification Search .............. 435/6; 536/23.1, 24.3
See application file for complete search history.

(56) References Cited

U.S. PATENT DOCUMENTS

| 6,174,670 | B1 | 1/2001 | Wittwer et al. | |
|---|---|---|---|---|
| 6,830,888 | B2 * | 12/2004 | Cockerill et al. | 435/6 |
| 2004/0146875 | A1 * | 7/2004 | Cotton et al. | 435/6 |
| 2005/0202470 | A1 * | 9/2005 | Sundberg et al. | 435/6 |

FOREIGN PATENT DOCUMENTS

| EP | 0 711 840 A | | 5/1996 |
|---|---|---|---|
| EP | 0 892 071 A | | 1/1999 |
| WO | WO 00/66777 A | | 11/2000 |
| WO | WO 02/066674 | * | 8/2002 |

OTHER PUBLICATIONS

Orita et al., PNAS 86 : 2766-2770 (Apr. 1989).*
Espejo et al., Microbiology 144 :1611-1617 (1989).*
Lipsky et al. Clinical Chemistry 47(4) : 635-644 (Apr. 2001).*
Frau et al. Bioconjugate Chemistry 8(2) : 222-231 (1997).*
Teare et al., Bio Techniques 22(6) :1170-1174 (1997).*
Anthony, et al., "Rapid Diagnosis of Bacteremia by Universal Amplification of 23S Ribosomal DNA followed by Hybridization to an Oligonucleotide Array," *J Clin Microbiol*, 38(2):781-788 (2000).
Avaniss-Aghajani, et al., "A Molecular Technique for Identification of Bacteria Using Small Subunit Ribosomal RNA Sequences," *Biotechniques*, 17(1):144-146, 148-149 (1994).
De Rijk, et al., "Compilation of small ribosomal subunit RNA sequences," *Nuc Acids Res*, 20 (Supplement):2075-2089 (1992).
Edwards, et al., "Isolation and direct complete nucleotide determination of entire genes. Characterization of a gene coding for 16S ribosomal RNA," *Nuc Acids Res*, 17(19):7843-7853 (1989).
Espejo, et al., "Page analysis of the heteroduplexes formed between PCR-amplified 16S rRNA genes: estimation of sequence similarity and rDNA complexity," *Microbiology*, 144:1611-1617 (1998).
Grimont, et al., "Ribosomal Ribonucleic Acid Gene Restriction Patterns as Potential Taxomomic Tools," *Ann Inst Pasteur Microbiol*, 137B(2):165-175 (1989).
Haugland, "*In Vitro* Application for Nucleic Acid Stains and Probes," *Handbook of Fluorescent Probes and Research Chemicals*, 6th ed., Molecular Probes Inc., Eugene OR, pp. 161-174 (1996).
Kulinski, et al., "Comparative calorimetric studies on the dynamic conformation of plant 5S rRNA: II structural interpretation of the thermal unfolding patterns for lupin seeds and wheat germ," *Nucleic Acids Res*, 19(9):2449-2455 (1991).
Lewin, *Genes V*, Chapter 5, "The Topology of Nucleic Acids," Oxford University Press and Cell Press: New York, p. 109-126 (1994).
Orita, et al., "Detection of Polymorphisms of Human DNA by Gel Electrophoresis as Single-Strand Conformation Polymorphisms," *PNAS*, 86:2766-2770 (1989).
Paner, et al., "Analysis of Melting Transitions of the DNA Hairpins formed from the Oligomer Sequences d[GGATAC(X)$_4$GTATCC] (X=A,T,G,C)" *Biopolymers*, 29:1715-1734 (1990).
Plato, "Differential Scanning Calorimetry as a General Method for Determining the Purity and heat of Fusion of High-Purity Organic Chemicals. Application to 95 Compounds," *Anal Chem*, 41(2):330-336 (1969).
Rantakokko-Jalave, et al., "Direct Amplification of rRNA Genes in Diagnosis of Bacterial Infections," *J Clin Microbiol*, 38(1):32-39 (2000).
Ririe, et al., "Product differentiation by analysis of DNA melting curves during the polymerase chain reaction," *Anal Biochem*, 245:154-160 (1997).
Santalucia, J., "A unified view of polymer, dumbbell, and oligonucleotide DNA nearest-neighbor thermodynamics," *PNAS USA*, 95:1460-1465 (1998).

(Continued)

*Primary Examiner*—Ethan Whisenant

(57) ABSTRACT

A novel method for characterizing nucleic acids. A nucleic acid is combined with a double stranded nucleic acid-specific dye to form a detectable complex between the dye and one or more double stranded structures within the nucleic acid. The combination is then exposed to varying temperatures and the fluorescence emission of the dye is measured to determine the melting temperature(s) for the double stranded structures. In some embodiments that melting temperature profile is then compared to melting temperature profiles generated for other nucleic acid(s) to discern differences between the compared nucleic acids.

43 Claims, 13 Drawing Sheets

OTHER PUBLICATIONS

Stubbs, et al., "PCR Targeted to the 16S-23S rRNA Gene Intergenic Spacer Region of *Clostridium* difficile and Construction of a Library Consisting of 116 Different PCR Ribotypes," *J Clin Microbiol*, 37:(2):461-463 (1999).

Vamosi, et al., "The helix-coil transition of DNA duplexes and hairpins observed by multiple fluorescence parameters," *Biochemistry*, 37:14300-14316 (1998).

Van Camp, "Amplification and Sequencing of Variable Regions in Bacterial 23S Ribosomal RNA Genes and Conserved Primer Sequence," *Curr Microbiol*, 27(3):147-151 (1993).

Van, N., et al., "Comparative Studies on the Secondary Structure of Ovalbumin Messenger RNA and its Complementary DNA Transcript," *Biochemistry, American Chemical Society*, 16(18):4090-4100 (1977).

Volker, et al., "High-resolution calorimetric and optical melting profiles of DNA plasmids: resolving contributions from intrinsic melting domains and specifically designed inserts," *Biopolymers*, 50:303-318 (1999).

Weisburg, et al., "16S ribosomal DNA amplification for phylogenetic study," *J Bacteriol*, 173(2):697-703 (1991).

Widjojoatmodjo, et al., "Rapid Identification of Bacteria by PCR-Single-Strand Conformation Polymorphism," *J Clin Microbiol*, 32(12):3002-3007 (1994).

Wittwer, et al., "The LightCycler™ : A Microvolume Multisample Fluorimeter with Rapid Temperature Control," *BioTechniques*, 22:176-181 (1997).

\* cited by examiner 9-12 Hairpin
5'- TATGCACTGTAAAAAATTACAGTGCGCTTAGGTCGAACACTCCTGTGTTCGACCTAGATAGG -3'

12 Tail
5'- TATTCGTGAGCAAACCTGACAGTGCGCTTAGGTCGAACACTCCTGTGTTCGACCTAGATAGG-3'

12 Hairpin
5'- TAGGTCGAACACTCCTGTGTTCGACCTA-3'

9 Tail
5'- TATGCACTGTAAAAAATTACAGTGCGCTCGTACGATAGACAACACGAGTCGACCTAGATAGC-3'

9 Hairpin
5'-GCACTGTAAAAAATTACAGTGC-3'

18 Hairpin    5'-GAGAGATAGGTCGAACACTCCTGTGTTCGACCTATCTCTC
15 Hairpin    5'-AGATAGGTCGAACACTCCTGTGTTCGACCTATCT
6 Hairpin     5'-TGACTGAAAACAGTCA
5 Hairpin     5'-GACTGAAAACAGTC
4 Hairpin     5'-ACTGAAAACAGT
3 Hairpin     5'-ACCAAAAGGT 9 Mismatch    5'-GCACTGTAAAAAATTACCGTGC 12 Mismatch   5'-TAGGTCGAACACTCCTGTGTTCTACCTA

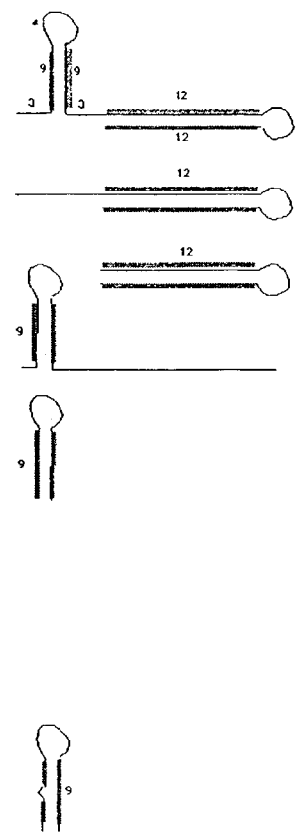

Figure 8.

```
                        SEQUENCE LISTING

<160> NUMBER OF SEQ ID NOS: 13

<210> SEQ ID NO 1
<211> LENGTH: 62
<212> TYPE: DNA
<213> ORGANISM: Homo sapiens

<400> SEQUENCE: 1
tatgcactgt aaaaaattac agtgcgctta ggtcgaacac tcctgtgttc gacctagata    60
gg                                                                  62

<210> SEQ ID NO 2
<211> LENGTH: 62
<212> TYPE: DNA
<213> ORGANISM: Homo sapiens

<400> SEQUENCE: 2
tattcgtgag caaacctgac agtgcgctta ggtcgaacac tcctgtgttc gacctagata    60
gg                                                                  62

<210> SEQ ID NO 3
<211> LENGTH: 28
<212> TYPE: DNA
<213> ORGANISM: Homo sapiens

<400> SEQUENCE: 3
taggtcgaac actcctgtgt tcgaccta                                      28

<210> SEQ ID NO 4
<211> LENGTH: 62
<212> TYPE: DNA
<213> ORGANISM: Homo sapiens

<400> SEQUENCE: 4
```

```
tatgcactgt aaaaaattac agtgcgctcg tacgatagac aacacgagtc gacctagata      60
gc                                                                    62

<210> SEQ ID NO 5
<211> LENGTH: 22
<212> TYPE: DNA
<213> ORGANISM: Homo sapiens

<400> SEQUENCE: 5
gcactgtaaa aaattacagt gc                                              22

<210> SEQ ID NO 6
<211> LENGTH: 40
<212> TYPE: DNA
<213> ORGANISM: Homo sapiens

<400> SEQUENCE: 6
gagagatagg tcgaacactc ctgtgttcga cctatctctc                           40

<210> SEQ ID NO 7
<211> LENGTH: 34
<212> TYPE: DNA
<213> ORGANISM: Homo sapiens

<400> SEQUENCE: 7
agataggtcg aacactcctg tgttcgacct atct                                 34

<210> SEQ ID NO 8
<211> LENGTH: 16
<212> TYPE: DNA
<213> ORGANISM: Homo sapiens

<400> SEQUENCE: 8
tgactgaaaa cagtca                                                     16

<210> SEQ ID NO 9
<211> LENGTH: 14
<212> TYPE: DNA
<213> ORGANISM: Homo sapiens

<400> SEQUENCE: 9
gactgaaaac agtc                                                       14

<210> SEQ ID NO 10
<211> LENGTH: 12
<212> TYPE: DNA
<213> ORGANISM: Homo sapiens

<400> SEQUENCE: 10
actgaaaaca gt                                                         12

<210> SEQ ID NO 11
<211> LENGTH: 10
<212> TYPE: DNA
<213> ORGANISM: Homo sapiens

<400> SEQUENCE: 11
accaaaaggt                                                            10

<210> SEQ ID NO 12
<211> LENGTH: 22
<212> TYPE: DNA
```

-continued

```
<213> ORGANISM: Homo sapiens

<400> SEQUENCE: 12
gcactgtaaa aaattaccgt gc                                              22

<210> SEQ ID NO 13
<211> LENGTH: 28
<212> TYPE: DNA
<213> ORGANISM: Homo sapiens

<400> SEQUENCE: 13
taggtcgaac actcctgtgt tctaccta                                        28
```

CHARACTERIZATION OF SINGLE STRANDED NUCLEIC ACIDS BY MELTING ANALYSIS OF SECONDARY STRUCTURE USING DOUBLE STRAND-SPECIFIC NUCLEIC ACID DYE

This application claims the benefit of U.S. Provisional Application No. 60/375,640, filed Apr. 26, 2002, the entire contents of which are hereby incorporated by reference.

GOVERNMENT FUNDING

This invention was made with government support under NIH grant number R41 GM 58983. The Government has certain rights to this invention.

SEQUENCE LISTING

The Sequence Listing submitted on compact disc is hereby incorporated by reference. The two identical compact discs contain the file named A70575 1.ST25. txt, created on Oct. 17, 2003, and containing 2,560 bytes.

FIELD OF THE INVENTION

The present invention relates to the identification and characterization of nucleic acids and modifications therein, which may be used to identify cells and/or organisms containing such nucleic acids and/or phenotypes or disease states associated with these nucleic acids or such modifications.

BACKGROUND OF THE INVENTION

Insights into secondary structure of nucleic acids have yielded powerful tools in mutation detection and organism identification. Several analytical techniques have been developed that take advantage of different secondary structures that exist between one sample and the next. Some of these techniques include Single-Stranded Conformational Polymorphisms (SSCP) (Orita et al., *PNAS (USA)* 86:2766–2770 (1989)), heteroduplex mobility assay (HMA) (Espejo et al., *Microbiology* 144:1611–1617 (1998)), ribotyping (Grimont and Grimont, *Ann. Inst. Pasteur Microbiol.* 137B(2):165–175 (1989)) and post-PCR product identification by product melting temperature ($T_m$) (Ririe et al., *Anal. Biochem.* 245154–160 (1997)).

Secondary structure analysis methods focus on detecting nucleic acid characteristics that depend on how specific sequences interact with each other. In 1989, Orita et al. demonstrated that a single base pair deletion or alteration is detectable by analyzing single-stranded conformational polymorphisms evident in nucleic acid gel electrophoresis (Orita, et al. 1989). Essentially, she found that small differences in the primary nucleic acid sequence result in slightly different secondary structure conformations, which migrate differentially in an electrophoresis gel matrix. SSCP analysis is very sensitive and even more specific than restriction fragment length polymorphism (RFLP) methods (Orita, et al 1989).

Similar to SSCP are Heteroduplex Mobility Assays or HMA. In HMA, the electrophoretic mobility of a non-perfectly matched DNA target-probe duplex is monitored (Espejo et al., 1998). The mismatching within the target-probe duplex causes secondary structure distortions resulting in mobility variations of the duplex. Differences in target sequences are therefore made evident by differential product migration in an electrophoresis gel matrix (Espejo et al., 1998).

Ribotyping is the identification of ribosomal nucleic acid gene restriction patterns observed by gel electrophoresis (Grimont and Grimont, 1989). Ribotyping takes advantage of the ubiquitous nature of ribosomes, the hypervariable regions found within their nucleic acid components and the specificity of restriction enzymes In this method, genes coding for rRNA, containing hypervariable regions flanked by conserved regions, are amplified using PCR and the DNA produced is subsequently enzymatically digested. Specific restriction enzymes are selected for restriction sites within the hypervariable regions. DNA cleavage by these enzymes results in small segments of DNA of varying lengths. Following enzymatic cleavage the DNA fragments are run on a gel and analyzed. A particular combination (pattern) of DNA segments is therefore indicative of the primary sequence. And if enzymes are chosen properly, each organism type will have a unique combination of restriction fragments (Grimont and Grimont, 1989; Van Camp, *Curr. Microbiol.* 27(3):147–151 (1993)).

Sequencing of ribosomal nucleic acids (rRNA) has identified many hypervariable regions surrounded by highly conserved regions (De Rijk et al., *Nuc. Acids Res.* 20 (Supplement):2075–2089 (1992); Edwards et al., *Nuc. Acids Res.,* 17(19):7843–7853 (1989); Grimont and Grimont, 1989; Van Camp, 1993). Indeed, many universal primer sites, capable of amplifying DNA from a wide variety of organisms, have been identified and adopted for SSCP or ribotyping analysis (Van Camp, 1993; Weisburg et al., *J. Bacteriol.* 173 (2):697–703 (1991); Stubbs et al., *J. Clin. Microbiol.* 37(2):461–463 (1999); Anthony et al., *J. Clin. Microbiol.* 38(2):781–788 (2000); Rantakokko-Jalava et al., *J. Clin. Microbiol.* 38(1):32–39 (2000); Widjojoatmodjo et al., *J. Clin. Microbiol.* 32(12):3002–3007 (1994)). Work performed by these research groups has found medically significant regions within the 16s and 23s genes that contain secondary structures within hypervariable segments. Van Camp and colleagues identified several universal primer sites which can be used to amplify hypervariable regions within the 23s gene (1993). The work done by Widjojoatmodjo demonstrates good species typing by SSCP with a small amplicon size, ranging from 108 bp to 300 bp (1994). And, Erik Avaniss-Aghajani et al. identified and tested a primer set "capable of amplifying the SSU [small subunit] rRNA from essentially all bacteria" for bacterial typing using ribotyping techniques (*Biotechiques.* 17(1):144–146, 148–149 (1994)).

In each of the analytical methods described above (SSCP, HMA and ribotyping), nucleic acid sequences are identified by secondary structural analysis. All three of these processes are highly sensitive to sequence variations and can be used to identify differences in nucleic acid sequences that exist between organisms. However, the assays all depend on gel electrophoresis, and ribotyping requires the additional step of enzymatic cleavage. Both gel electrophoresis and enzymatic cleavage are time-consuming post-amplification steps.

In another form of secondary structural analysis of nucleic acids, primary sequence variations are made evident by observing double stranded nucleic acid melting characteristics. Melting of nucleic acids refers to the conformational transition from a doublehelical state to a single-stranded state. The temperature at which half of the nucleic acid strands are in the doublehelical state and half are in the 'random coil' (single stranded) state is defined as the melting temperature ($T_m$). (Santa Lucia, *PNAS (USA)* 95:1460–1465

(1998)). The $T_m$ of a given pair of nucleic acid strands therefore, is indicative of the stability of the strand to strand binding and depends on the strands' complementarity, sequence length, GC content and environmental conditions (Lewin, *Genes V*, Chapter 5, Oxford University Press and Cell Press: New York, (1994) pp. 109–126; SantaLucia, 1998).

The analysis of nucleic acid melting has been accomplished in many ways. Methods to observe and analyze nucleic acid denaturation transitions include: measuring the enthalpy change within a sample as it denatures by differential scanning calorimetry (DSC) (Kulinski et al., *Nucleic Acids Res.* 19(9):2449–2455 (1991); Paner et al., *Biopolymers* 29:1715–1734 (1990); Volker et al., *Biopolymers* 50:303–318 (1999)), measuring the fluorescence of covalently attached pairs of fluorophores (Vamosi and Clegg, *Biochemistry* 37:14300–14316 (1998)), and monitoring the change in hyperchromicity of nucleic acids (Haugland, "In Vitro Applications for Nucleic Acid Stains and Probes", in *Handbook of Fluorescent Probes and Research Chemicals*, 6$^{th}$ ed., Molecular Probes Inc, Eugene OR (1996) pp. 161–174). DSC is a technique which was first used to measure the purity of a chemical. The process measures the heat evolved or absorbed during chemical reactions or transitions (Plato, *Anal. Chem.* 41(2):330–336 (1969)). Detailed analysis and development of theoretical models of nucleic acid transitions have been possible using DSC techniques (Paner et al., 1990). Kulinski observed different melting profiles of two plant 5S rRNA segments obtained from Lupin seeds and Wheat germ using DSC (Kulinski, 1991). Unfortunately, both optical (hyperchromicity) and DSC analyses requires a substantial quantity of nucleic acid, analysis is slow and usually only single samples can be studied at a time. And, the measure of fluorescence resonance energy transfer between paired fluorophors, as described in Vamosi and Clegg (1998), requires the covalent attachment of the fluorophors at termini of duplexed nucleic acid, which termini must be adjacent when the nucleic acid is duplexed for effective measurement.

$T_m$ values of double stranded nucleic acids can also be observed by monitoring the fluorescence of double-stranded DNA-specific dyes combined with the nucleic acids (Wittwer et al., 1996). Double stranded-specific dyes are nucleic acid-binding fluorophores. Typically, the fluorescence of these dyes increases when bound to duplexed nucleic acids (Wittwer et al., *BioTechniques* 22:176–181 (1997)). Ririe et al. (1997) demonstrated that post PCR products can be differentiated by melting curve analysis using the double stranded nucleic acid binding dye SYBR® Green I. SYBR® Green I binds preferentially to double stranded nucleic acid (Haugland, 1996).

The process of $T_m$ analysis does not require additional post-PCR handling. However, current applications using double stranded DNA-specific dyes, such as SYBR Green I, are not sequence specific and have not been used to differentiate organisms with one primer set. Furthermore, these dyes have only been used in the analysis of separate, complementary strands of nucleic acid.

In light of the foregoing discussion, it is apparent that there is a need for faster and simpler methods of analysis of single stranded nucleic acid. Such methods should be applicable to both identifying variations in a sequence, such as SSCP and HMA, and typing organisms, such as ribotyping.

SUMMARY OF THE INVENTION

In accordance with the foregoing, the present invention provides methods for characterizing nucleic acids wherein a single stranded form of the nucleic acid is combined with a double stranded nucleic acid-specific dye and the combination is exposed to varying temperatures to generate a melting temperature profile for double stranded secondary structures which reversibly form within the single stranded nucleic acid.

In a preferred embodiment, the double stranded nucleic acid-specific dye is selected from the group consisting of SYBR® Green I, SYBR® Gold, ethidium bromide, propidium bomide, Pico Green, Hoechst 33258, YO-PRO-1 and YO-YO-1.

In an additional preferred embodiment, the melting temperature profile of one nucleic acid is compared to the melting temperature profile of a second nucleic acid, wherein a difference in the profiles indicates a difference in sequence between said first and second nucleic acids.

In another preferred embodiment, the present invention provides a method for detecting a mutation in a nucleic acid. In this embodiment, the melting temperature profile of a single stranded nucleic acid sample is determined using a double stranded nucleic acid-specific dye, and differences between the melting temperature profile of the nucleic acid sample and the wild-type nucleic acid melting temperature profile indicates the presence of one or more mutations in the nucleic acid sample within in one or more regions in the single stranded nucleic acid which are capable of reversibly forming a double stranded secondary structure.

In a further preferred embodiment, the present invention provides a method of identifying the species type of a cell. In this embodiment, the melting temperature profile of a sample rRNA, or fragment thereof from a cell, is determined using a double stranded nucleic acid-specific dye. The profile is then compared to known rRNA profiles for one or more cells and a match indicates that the sample rRNA is from the known rRNA cell type. Such cells may be animal, bacterial, or plant cells.

In another preferred embodiment, the single stranded nucleic acid is derived from an amplified gene or fragment thereof.

In a further preferred embodiment, the amplified sample rRNA is produced by a method selected from the group consisting of strand displacement amplification (SDA), polymerase chain reaction (PCR) amplification, rolling circle amplification (RCA), nucleic acid sequence based amplification (NASBA), transcription mediated amplification (TMA), asymmetrical PCR amplification, and ligase chain reaction (LCR) amplification.

In an additional preferred embodiment, the determination of melting temperature profiles are accomplished by combining a single stranded nucleic acid sample with a double stranded nucleic acid-specific dye to form a detectable complex between the dye and one or more double stranded secondary structures which form within said nucleic acid and measuring fluorescence emission of the dye while varying the temperature.

In another aspect of this invention, various fluorescent dyes are identified for secondary structure detection. These dyes were initially identified for use in PCR applications. These "saturation dyes" are capable of existing at sufficiently saturating conditions with respect to the DNA during or after amplification, while minimizing the inhibition of PCR. For example, at maximum PCR-compatible concentrations, the dsDNA binding dye has a percent saturation of at least 50%. In other embodiments, the percent saturation is at least 80%, and more particularly, at least 90%. In yet other embodiments, the percent saturation is at least 99%. It is understood that the percent saturation is the percent fluorescence compared to fluorescence of the same dye at saturating concentrations, i.e. the concentration that provides the highest fluorescence intensity possible in the presence of a predetermined amount of dsDNA. Because these dyes can be present at significantly higher concentrations without significantly interfering with certain nucleic acid reactions, it is believed that these dyes may be particularly useful for monitoring the conformation of single-stranded nucleic acids.

DESCRIPTION OF THE DRAWINGS

FIG. 8 is an illustration of both the exact sequences and proposed secondary structures for all 13 model oligonucleotides used (SEQ ID NOS:1–13). Shaded regions under the sequences on the left identify the sequences involved in the hairpin formation on the right. Sequence lengths range from 10 nucleotides to 56 nucleotides. Oligos are named by hairpin lengths and also indicate the presence of modifications such as tails or mismatches. The oligo named 9–12 Hairpin, contains two hairpins forming double stranded domains of 9 bp and 12 bp.

DETAILED DESCRIPTION OF THE INVENTION

Figure 1:
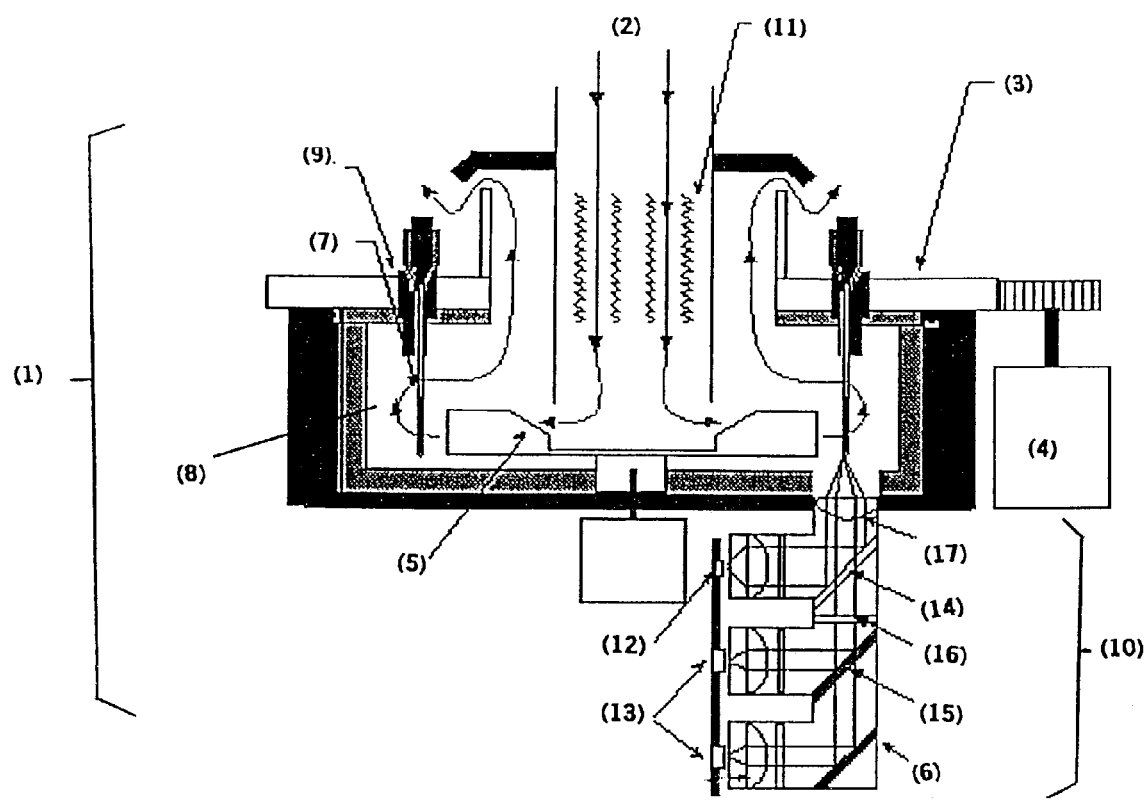
FIG. 1 depicts the components of a standard two-color LightCycler used for rapid DNA amplification and analysis by PCR and fluorescent monitoring. The instrument (1) consists of an air inlet (2), a circular sample carousel (3), stepper motor (4), chamber fan (5), and optics/filter assembly (6). Samples (7) are placed within glass capillaries and maintained in a vertical sample alignment within the reaction chamber (8) with twenty-four brass offset guides (9). The stepper motor (4) is used to rotate the sample carousel (3) and position samples (7) over the excitation and collection optics (10). Rapid temperature cycling is achieved by employing high-wattage heating coils (11) and continuous airflow. The general movement of air through the chamber is indicated by arrows and is driven by the rotation of the fan (5). The use of glass capillaries increases the thermal transfer rates into the sample (7) and also affords total internal reflectance for enhanced fluorescent monitoring. Fluorophores present in the reaction mixture are then excited and monitored by epi-illumination of the capillary tip. A blue LED (12) is used for excitation and two photo diodes (13) are employed for fluorescent monitoring. The filter assembly (6) contains two dichroics (14–15), with the indicated nanometer cut offs, to separate fluorescence emission into two channels (16–17) for data collection.

The present invention provides methods for analysis of single stranded nucleic acids having secondary structure which manifests in regions of double strandedness. A nucleic acid molecule containing both single and double stranded segments will have a specific measurable melting temperature or $T_m$ for each of the double stranded nucleic acid sections. The invention shows for the first time that the melting transitions of the double stranded segments can be determined by monitoring fluorescence intensity of double stranded nucleic acid-specific (dsNA-S) dyes. Furthermore, the invention shows that if species-specific sequence variations within the double stranded regions exist, species-dependent melting profiles can be obtained. This analytical technique, performing secondary structural analysis by monitoring nucleic acid melting transitions, is capable of distinguishing non-identical nucleic acids, such as altered or mutated nucleic acids and nucleic acids not so altered or mutated. Homologous nucleic acids having species-specific sequences, such as ribosomal RNA or the genes encoding them, may be used to identify the species of a cell from which such nucleic acid is taken. Furthermore, amplified nucleic acids may be characterized using the present invention without the normal post-amplification processing required by known techniques.

Accordingly, provided herein are methods for characterizing a single stranded nucleic acid. This characterization entails monitoring changes in secondary structure of the single stranded nucleic acid in response to changes in the nucleic acid's environmental temperature. More specifically, the methods involve determining the melting temperature ($T_m$) of double stranded or apparent double stranded regions resulting from the secondary conformation of the single stranded nucleic acid. Double stranded nucleic acid-specific dyes are used to monitor these transitions in secondary structure in response to varying temperature. Without being bound by theory, double stranded regions form due to hydrogen bonding and other noncovalent interactions between different segments of the single stranded nucleic acid, largely through hybridization between complementary and nearly complementary regions. A double stranded region of a single stranded nucleic acid, as described above, is referred to herein as a "double stranded secondary structure".

In the broadest sense, by "nucleic acid", "polynucleotide" or "oligonucleotide" or grammatical equivalents herein means at least two nucleotides covalently linked together. Nucleic acids susceptible to the analysis of the invention have sufficient complementarity between at least two regions of the linear sequence and have sufficient length to form at least one double stranded secondary structure. Nucleic acids will generally consist of naturally occurring nucleotides. However, the skilled artisan will recognize that the invention is applicable to nucleic acids which are DNA, both genomic and cDNA, RNA or a hybrid, where the nucleic acid sequence contains any combination of deoxyribo- and ribo-nucleotides, and any combination of bases, including uracil, adenine, thymine, cytosine, guanine, inosine, xanthine hypoxanthine, isocytosine, isoguanine, etc. As used herein, the term "nucleoside" includes nucleotides and nucleoside and nucleotide analogs, and modified nucleosides such as amino modified nucleosides. In addition, "nucleoside" includes non-naturally occurring analog structures. Thus for example the individual units of a peptide nucleic acid sequence, each containing a base, are referred to herein as a nucleoside.

A nucleic acid sequence of the present invention will generally contain phosphodiester bonds, although the skilled artisan will appreciate that the invention is applicable to nucleic acid analogs that may have alternate backbones, comprising, for example, phosphoramidate (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989)), O methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids which may be analyzed using the invention include those with positive backbones (Denpcy et al., Proc. Natl. Acad. Sci. USA 92:6097 (1995); nonionic backbones (U.S. Pat. Nos. 5,386,023, 5,637,684, 5,602,240, 5,216,141 and 4,469,863; Kiedrowski et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within one definition of nucleic acids (see Jenkins et al., Chem. Soc. Rev. (1995) pp169–176). Several nucleic acid analogs are described in Rawls, C & E News Jun. 2, 1997 page 35. All of these references are hereby expressly incorporated by reference.

As will be appreciated by those in the art, all of these nucleic acid analogs may find use in the present invention. In addition, mixtures of naturally occurring nucleic acids and analogs can be analyzed using the invention, as well as mixtures of different nucleic acid analogs, and mixtures of naturally occurring nucleic acids and analogs.

In a preferred embodiment of the invention, single stranded nucleic acid is combined with double stranded nucleic acid-specific dye. By "combine" and grammatical equivalents thereof is meant that the nucleic acid and dye are made to be in sufficiently close proximity to interact. For example, the nucleic acid and dye may be added to the same solution, simultaneously or sequentially in either order. As the skilled artisan will recognize, in particular from the discussion below, the single stranded nucleic acid may be produced in the presence of the dye, for example when the nucleic acid is an amplification product. Production of one component in the presence of another is also encompassed by the term "combine", as used herein.

Double stranded nucleic acid-specific dyes are well known in the art. In general, a dsNA-S dye is any substance that is capable of being detected when in the presence of, preferably complexed with, a double stranded nucleic acid. Typically, a dsNAS dye will preferentially bind or complex with double stranded nucleic acid.

Preferably, the dsNA-S dye is a fluorescent dye, and its fluorescent characteristics when complexed with the double stranded nucleic acid is distinguishable from when it is not so complexed. Typically, a dsNA-S dye will produce a stronger (larger) fluorescent signal (fluorescent emmission) when complexed with the double stranded nucleic acid than when it is not. However, such dyes may produce a weaker (smaller) fluorescent signal when bound to double stranded nucleic acid, or they may produce a different fluorescent signal, such a signal at a different wave length. Any such differentiable signal is useful in the present invention.

Dyes useful in the methods disclosed herein include, but are not limited to, SYBR® Green I, SYBR® Gold, ethidium bromide, acridine orange, propidium bromide, PicoGreen®, Hoechst 33258, Hoechst 33342, Hoechst 34580, YO-PRO®-1 and YOYO®-1. Each of these dyes is commercially available. For example, Chapter 8 of the Molecular Probes (Eugene, Oreg.) catalog *Handbook of Fluorescent Probes and Research Products*, Eighth Edition (on CD-ROM, May, 2001; incorporated herein by reference) lists a host of dyes that may be used in the present invention.

Saturation dyes may also be used in the methods of the instant invention. Many saturation dyes belong to a family of cyanines. However, it is contemplated that other families of dsDNA binding dyes are useful, including but not limited to phenanthridinium intercalators and phenanthroline-based metallointercalators. Cyanine dyes useful in the present method include, but are not limited to, LightCycler Green and PO-PRO-1, BO-PRO-1, SYTO 43, SYTO 44, SYTO 45, POPO-1, POPO-3, BOBO-1, and BOBO-3 (Molecular Probes), which are monomers or dimers of unsymmetrical cyanines with a pyridinium core structure generally described as:

Formula I

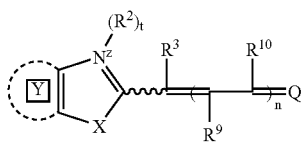

wherein
the moiety Y forms an optionally-substituted fused mono or polycyclic aromatic or nitrogen-containing heteroaromatic ring;

X is oxygen, sulfur, selenium, tellurium, or a group selected from $C(CH_3)_2$, and $NR^1$, where $R^1$ is hydrogen or $C_{1-6}$ alkyl;

$R^2$ is an optionally-substituted $C_{1-6}$ alkyl, or a cyclic or acyclic heteroatom-containing moiety. Illustrative heteroatom-containing moieties include optionally substituted heteroalkyl, heterocyclyl, sulfonate, amino, carboxy, heteroalkenyl, heteroallyl, esters, amine, amide, phosphorusoxygen, and phosphorus-sulfur bonds. Illustrative heteroatom-containing moieties are discussed in U.S. Pat. No. 5,658,751 and WO 00/66664, herein incorporated by reference.

t=0 or 1;

z is a charge selected from 0 or 1, providing that z=t;

$R^3$, $R^9$, and $R^{10}$ are independently selected from hydrogen and $C_{1-6}$ alkyl;

n=0, 1, or 2;

Q is an aromatic ring selected from the group of structures consisting of:

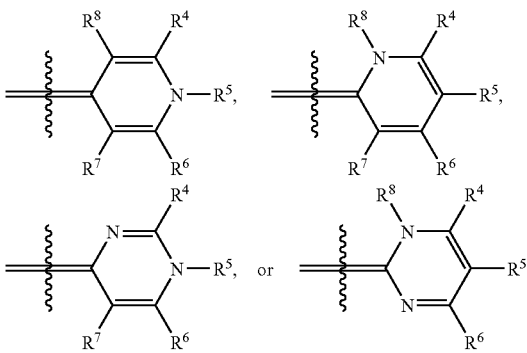

wherein $R^4$, $R^5$, $R^6$, $R^7$, and $R^8$ are independently selected from the group consisting of hydrogen; halogen; alkyl, cycloalkyl, heteroalkyl, heterocycloalkyl, alkenyl, polyalkenyl, alkynyl, polyalkynyl, aryl, heteroaryl, cycloalkyl, all optionally substituted; other heteroatom-containing moiety; BRIDGE-DYE (including dimers); and a reactive group, each optionally including a charged group such as a quaternary ammonium. BRIDGE is defined in WO 00/66664, already incorporated by reference. DYE is a compound of Formula I. Stereoisomers are included in the description of cyanine dye structures unless specifically excluded.

Illustrative dyes for use in the present invention are cyanine dyes of Formula I having a pyridinium or pyrimidinium core structure wherein the moiety Y forms an optionally-substituted benzene, thereby forming a benzazolium ring; X is oxygen or sulfur; n=0 or 1; t=0 or 1; $R^2$ is methyl; Q is an aromatic ring selected from the group of structures consisting of:

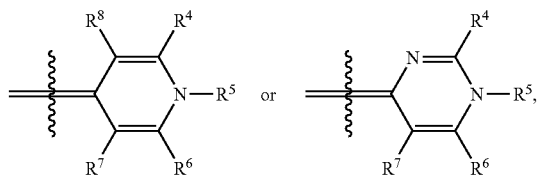

and preferably Q is:

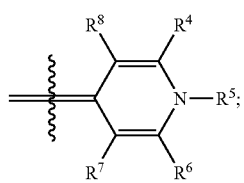

wherein
$R^4$ is hydrogen, alkoxy (such as OMe), alkylthio (such as SMe), or heterocycloalkyl (such as piperazinyl), or heterocycloalkyl including a charged group (such as 4,4-dimethylpiperazinium-1-yl);

$R^5$ is $C_{1-6}$ alkyl, (such as Me), or phenyl, $(CH_2)_3N^+(Me)_3$, or $(CH_2)_3N^+Me_2(CH_2)_3N^+Me_2(CH_2)_3$ that is additionally connected to the nitrogen of a second 4-pyridinium, thereby forming a dimer, where the second pyridinium is part of a second compound of Formula I; and $R^6$, $R^7$, and $R^8$ are hydrogen.

Unsymmetrical cyanines with a quinolinium core structure such as, but not limited to, LO-PRO-1, JO-PRO-1, YO-PRO-1, TO-PRO-1, SYTO 11, SYTO 13, SYTO 15, SYTO 16, SYTO 20, SYTO 23, TOTO-3, YOYO-3 (Molecular Probes, Inc.), GelStar (Cambrek Bio Science Rockland Inc., Rockland, Me.), and thiazole orange (Aldrich) are also useful The quinolinium core structure issimilar to that of pyridinium-based cyanines, except that either a 4-quinolinium (shown below as Formula II) or a 2-quinolinium occupies the right portion of the molecule instead of a pyridinium.

Formula II

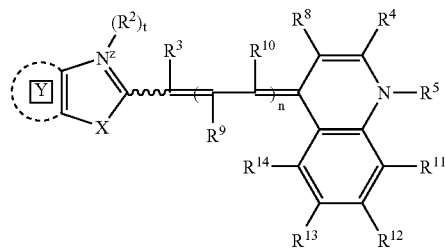

wherein
the moiety Y forms an optionally-substituted fused mono or polycyclic aromatic or nitrogen-containing heteroaromatic ring;

X is oxygen, sulfur, selenium, tellurium, or a group selected from $C(CH_3)_2$, and $NR^1$, where $R^1$ is hydrogen or $C_{1-6}$ alkyl;

$R^2$ is an optionally-substituted $C_{1-6}$ alkyl, or a cyclic or acyclic heteroatom-containing moiety.

t=0 or 1;

z is a charge selected from 0 or 1, providing that z=t;

$R^3$, $R^9$, and $R^{10}$ are independently selected from hydrogen and $C_{1-6}$ alkyl;

n=0, 1, or 2;

and $R^4$, $R^5$, $R^8$, $R^{11}$, $R^{12}$, $R^{13}$, and $R^{14}$ are independently hydrogen; halogen; alkyl, cycloalkyl, heteroalkyl, heterocycloalkyl, alkenyl, polyalkenyl, alkynyl, polyalkynyl, aryl, heteroaryl, cycloalkyl, all optionally substituted; other heteroatom-containing moiety; and a reactive group, each optionally including a charged group such as a quaternary ammonium, provided that $R^4$ is a moiety with molecular weight of less than 115, and more preferably less than 105. Alternatively, $R^4$, $R^8$, $R^{11}$, $R^{12}$, $R^{13}$, and $R^{14}$ are as defined above, and two compounds of Formula II are taken together to form a dimer, where each of the groups $R^5$ of Formulae II are taken together to form a divalent moiety, provided that if the dye is a dimer of a quinolinium cyanine n=1 or 2.

Illustrative dyes for use in the present invention include cyanine dyes of Formula II wherein the moiety Y forms an optionally-substituted benzene, thereby forming a benzazolium ring; X is oxygen or sulfur; n=0 or 1; t=0 or 1; R2 is methyl;

$R^4$ is hydrogen, $C_{1-6}$ alkyl (such as Me), or optionally-substituted phenyl, preferably phenyl;

$R^5$ is $C_{1-6}$ alkyl, (such as methyl), or optionally-substituted phenyl, preferably phenyl; and $R^8$ is hydrogen, and $R^{11}$, $R^{12}$, $R^{13}$, and $R^{14}$ are hydrogen or alkoxy (such as methoxy).

Illustrative dyes for use in the present invention also illustratively include cyanine dyes of Formula II wherein the moiety Y forms an optionally-substituted heterocycle (such as 1-methylpyridinium or 3-bromo-1-methylpyridinium); X is oxygen or sulfur; n=0 or 1; t=z=0;

$R^4$ is hydrogen or $C_{1-6}$ alkyl (such as Me);

$R^5$ is $C_{1-6}$ alkyl, (such as Me), optionally-substituted phenyl, preferably phenyl or heteroalkyl including a charged group (such as the group —$(CH_2)_3N(Me)_3$); and $R^8$ is hydrogen, and $R^{11}$, $R^{12}$, $R^{13}$, and $R^{14}$ are hydrogen, alkyl (such as methyl), or alkoxy (such as methoxy).

It is understood that the above cyanine dyes are illustrative, and other cyanine dyes may be useful in the presently-described methods.

Some quinolinium-based unsymmetrical cyanines, including SYBR® Green I, are not included within the definition of "saturation dyes." When the dye is a monomer of a quinolinium-based cyanine, it is possible that bulky substitutions on the carbon next to the nitrogen of the quinolonium ring (position equivalent to $R^4$) interfere with the dye's ability to bind at high saturation levels. Bulky substitutions are, for example, long branched hetero-atom-containing aliphatic chains or aromatic moieties substituted with aliphatic branches that are larger than MW=105. This restriction, however, does not apply to pyridinium cyanines mentioned earlier. In the case of quinolinium-based cyanine dimers, the length between the left and right ring systems (determined by the group —$CR^3(=CR^9-CR^{10})_n=$) also appears to determine functionality. While these dyes are not included within the definition of "saturation dyes" and may not be suitable for certain applications, dyes such as SYBR® Green I are compatible with the methods of the present disclosure.

In a preferred embodiment, combination of the single stranded nucleic acid and the dsNA-S dye results in the formation of a detectable complex between the dye and one or more double stranded secondary structures within the nucleic acid. Without being bound by theory, the dsNA-S dye has a preferential affinity for the double stranded nucleic acid and binds or otherwise joins with the double stranded nucleic acid, frequently by intercalating between the two strands of nucleic acid. The joining of the dye and the nucleic acid results in dye being differentiable from dye not so joined with double stranded nucleic acid. Therefore, as used herein, by "detectable complex" is meant a double stranded secondary structure of a single stranded nucleic acid and a dsNA-S dye joined to form a complex that is differentiable from dsNA-S dye not joined with a double stranded secondary structure.

Preferably, the dsNA-S dye is a fluorescent dye. Preferably, detection is by measurement of fluorescent emission from the dsNA-S dye. Generally, a fluorophor produces fluorescent emission (photon emission) at a specific frequency or band of frequencies in response to exposure to a specific frequency or band of frequencies referred to as an "excitation" wavelength. In the present invention, each dsNA-S dye produces a fluorescent emission when joined with the double stranded secondary structure in the detectable complex that is distinguishable from when the dye is not in the detectable complex. Preferably, the emission of the dye in the detectable complex is distinguishable by strength of the emission and/or by spectral content of the emission. In some cases, the dye has virtually no fluorescent emission when not in the detectable complex. Typically, the emission of the dye is greater (stronger) when in the detectable complex; however, formation of the detectable complex may reduce the emission of some dyes and/or alter the spectral content of the emission.

Measurement of fluorescent emission (luminescence) from fluorophors, such as fluorescent dsNA-S dyes, is well known in the art. Typically, excitation illumination is provided to a sample containing a fluorophor and the emission at a frequency or frequency band of interest is measured using one or more filters and an optical detector, for example a photodiode.

In a preferred embodiment of the invention, the temperature of the single stranded nucleic acid being analyzed is varied. By "varying the temperature" is meant increasing and/or decreasing the temperature. In a preferred embodiment, the single stranded nucleic acid is provided at a temperature below the melting temperature (as defined below) of one or more of its double strand secondary structures and increased to a temperature above the $T_m$ of the double strand secondary structures. Many means of varying the temperature of a nucleic acid sample are known and available in the art.

In a preferred embodiment of the invention, the temperatures between which the variation occurs are about 10° and 100° C., more preferably between about 20° and 95° C. and still more preferably between about 30° and 95° C.

In a preferred embodiment, the temperature of the single stranded nucleic acid is varied at a rate of between about 0.005° and 0.05° C./sec, more preferably between about 0.001° and 0.1° C./sec, still more preferably between about 0.0001° and 1° C./sec. In an especially preferred embodiment, the temperature of the single stranded nucleic acid is varied at a rate of about 0.01° C./sec or less.

In a preferred embodiment, the melting temperature ($T_m$) of one or more double stranded secondary structures of the single stranded nucleic acid is determined. In general, melting of nucleic acids refers to the conformational transition from a double-helical state to a single-stranded state. The temperature at which half of the nucleic acid strands are in the doublehelical state and half are in the 'random coil' (single stranded) state is defined as the melting temperature ($T_m$) (Santa Lucia, *PNAS (USA)* 95:1460–1465 (1998)). The $T_m$ of a given pair of nucleic acid strands therefore, is indicative of the stability of the strand to strand binding and depends on the strands' complementarity, sequence length, GC content and environmental conditions (Lewin, *Genes V*, Chapter 5, Oxford University Press and Cell Press: New York, (1994) pp. 109–126; Santa Lucia, 1998). As used herein, with regard to a double stranded secondary structure of single stranded nucleic acid, "melting temperature", "$T_m$" and grammatical equivalents thereof is meant the temperature at which approximately half of the single stranded nucleic acids of a sample comprise the double stranded secondary structure and approximately half do not, due to dissociation of the two segments of the single stranded nucleic acid which formed the double stranded secondary structure.

As discussed in the Background section, many methods of determining melting temperature of a nucleic acid are known in the art. In a preferred embodiment, $T_m$ of a double stranded secondary structure of a single stranded nucleic acid is determined by monitoring the fluorescent emission of dsNA-S dye combined with the single stranded nucleic acid while varying the temperature of the nucleic acid. A change in fluorescent emission at a given temperature or limited temperature range indicates a melting temperature of a double stranded secondary structure.

As the skilled artisan will appreciate, the melting of any double stranded nucleic acid structure generally occurs in a substantial proportion of a population of similar nucleic acids over a limited temperature range and will typically have a peak of melting (most rapid transition) at approximately the $T_m$ for that nucleic acid. Therefore, such peaks of change in fluorescence emission can be used to calculate the $T_m$ for double stranded secondary structures.

Furthermore, any single stranded nucleic acid having one or more double stranded secondary structures will provide a characteristic $T_m$ profile. By "$T_m$profile", "melting temperature profile", and grammatical equivalents thereof, is meant a description of the relative amount of a single stranded nucleic acid having double stranded secondary structures. In a preferred embodiment, a $T_m$ profile is generated by measuring the fluorescent emission of a dsNA-S dye to indicate the amount of dye incorporated in a detectable complex with double stranded secondary structures, thus indicating the amount of the single stranded nucleic acid that is in a double stranded conformation.

A melting temperature profile may be graphically represented by plotting $-dF/dT$ against T, where dF is the change in measured fluorescence emission, dT is the change in temperature of the nucleic acid, and T is the temperature of the nucleic acid.

Such a graphic representation will show peaks at temperatures at which the most rapid changes in fluorescence occur, indicating melting temperatures.

The single strand nucleic acid to be analyzed for $T_m$ of double strand secondary structures may be part of or isolated from a primary a sample from any source, such as nucleic acid from a cell or tissue sample. The nucleic acid may be a synthetic nucleic acid. The nucleic acid to be analyzed may also be a nucleic acid amplification product. Of course, the nucleic acid to be amplified may be obtained from any source, either naturally occurring or synthesized.

By "nucleic acid amplification product", "amplification product", "amplified nucleic acid" and grammatical equivalents thereof is meant the product of a nucleic acid amplification method whereby copies of an initial nucleic acid are made. The skilled artisan will appreciate that there are many methods available to amplify a nucleic acid. Perhaps the most popular method is polymerase chain reaction (PCR; for example, see, U.S. Pat. Nos. 4,683,195 and 4,683,202, as well as Saiki et al., *Science* 230:1350–1354 (1985) and Gyllensten et al., *PNAS (USA)* 85:7652–7656 (1985)). A preferred variation of the PCR method is asymmetrical PCR (for example, see Mao et al., *Biotechniques* 27(4):674–678 (1999); Lehbein et al., *Electrophoresis* 19(8–9):1381–1384 (1998); Lazaro et al., *Molec. Cell. Probes* 6(5):357–359 (1992); and U.S. Pat. No. 6,197,499). Other amplification methods include, but are not limited to, strand displacement amplification (SDA) (see, Walker et al., *Nuc. Acids Res.* 20(7):1691–1696 (1992), as well as U.S. Pat. Nos. 5,744,311, 5,648,211 and 5,631,147), rolling circle amplification (RCA) (see PCT publication WO 97/19193), nucleic acid sequence-based amplification (NASBA) (see Compton, *Nature* 350:91–92 (1991); as well as U.S. Pat. Nos. 5,409,818 and 5,554,527), transcript mediated amplification (TMA) (see Kwoh et al., *PNAS (USA)* 86:1173–1177 (1989), as well as U.S. Pat. No. 5,399,491), self sustained sequence replication (3SR) (see Guatelli et al., *PNAS (USA)* 87:1874–1879 (1990) and ligase chain reaction (LCA) (see U.S. Pat. Nos. 5,427,930 and 5,792,607).

In one preferred embodiment, the nucleic acid to be analyzed is a naturally occurring nucleic acid obtained or isolated from a cell or tissue sample. In another preferred embodiment, the nucleic acid is amplified nucleic acid. In the latter embodiment, preferably the amplified nucleic acid is a product of PCR, more preferably a product of asymmetrical PCR.

The present invention finds many applications. For example, a $T_m$ profile may be used to characterize a single stranded nucleic acid. Such characterization may then be used to compare different single strand nucleic acids. A difference in the $T_m$ profile of two nucleic acids indicates that the two nucleic acids have different sequences. Identification of differences in the sequence between two nucleic acids has many uses.

In one embodiment, an alteration in a sequence of a sample nucleic acid may be detected by comparing the $T_m$ profile of the sample nucleic acid to that of a nucleic acid having a known sequence. For example, the $T_m$ profile of a nucleic acid of known sequence from the genome of a normal or standard cell may be determined.

The $T_m$ profile of a similar nucleic acid from a sample of the same cell type may be determined. A difference between the $T_m$ profiles of the nucleic acid from the normal/standard cell and the nucleic acid from the sample indicates an allelic variation or a mutation in the nucleic acid from the sample. Furthermore, the $T_m$ profile of the nucleic acid from the sample can indicate the nature of the difference from the normal/standard nucleic acid, if profiles of known sequence variations have been determined. Using this technique, individuals may be typed for specific alleles or screened for diseases caused by specific mutations.

Another use for $T_m$ profile determinations of nucleic acid samples from cells is determination of the species type of the cell from which the sample was taken. Particularly useful for such determinations are ribosomal RNA or, preferably, amplified regions of DA encoding ribosomal RNA. As discussed in the Background section, many hypervariable regions surrounded by highly conserved regions in the sequences of ribosomes have been identified, the hypervariable regions being species-specific. And primers based on the conserved regions have been developed to specifically amplify such hypervariable regions for ribotyping techniques. The present invention can be used in a similar fashion to type cells from which a nucleic acid sample is obtained by amplifying segments (e.g., endonuclease digestion fragments) of ribosomal nucleic acid in the sample and determining the $T_m$ profile for such amplification products. Comparing the $T_m$ profile with $T_m$ profiles from similar nucleic acid segments from known species can show the species from which the sample is obtained. These methods may be used, for example, to identify the cause of an infection or to identify the presence of an infectious cell type.

The present invention finds uses in many fields, including but not limited to genetics, immunology, infectious disease, oncology, epidemiology and forensics. Such uses include, but are not limited to, identifying mutations in tumorigenic material, identifying inheritable genetic disease and guiding treatment for such diseases. Additionally, the invention may be used for identifying allelic variants, identifying sources of biological samples and determining paternity.

It will be apparent to one of ordinary skill in the art that many other applications of the present invention are possible. All references cited herein are incorporated in their entirety.

The following examples are provided for illustrative purposes. It is understood that these examples in no way serve to limit the true scope of the invention.

EXAMPLES

Example 1

Modification of a Rapid Thermal Cycling Device Having Fluorescence Detection Capabilities for the Production of Sample Temperatures in the Range of 20° C. to 100° C.

The LightCycler™ (Idaho Technologies, Idaho Falls, Id.) was selected as the instrument of choice for the experiments described herein, due to its fluorescence monitoring capabilities and small sample volumes. However, a review of the literature pertaining to melting temperatures of nucleic acids suggested that a broader range of temperatures would be needed than the standard range of 40° C. to 100° C. of the LightCycler™. For example, the standard lengths of double-helical regions within ribosomal genes were known to range from around 3 bp to 20 bp (De Rijk et al., supra; Gutell et al., *Nucleic Acids Res.* 21(13):3055–3074 (1993); Specht et al., *Nucleic Acids Res.* 25(1):96–97 (1997); Szymanski et al., *Nucleic Acids Res.* 28(1):166–167 (2000)). Kulinksi et al. (1991) found that 5S rRNA samples from both Wheat Germ and Lupin seeds had observable transitions between 300 and 340 K (27° and 67° C.), and very distinct melting transition profiles were observed for the two specimens. Paner et al. reported a 55° C.-centered transition for a hairpin containing a 6 bp stem with a 4 bp loop (1990). Vamosi and Clegg recorded a melting range of 20° to 71° C. for hairpins ranging in stem sizes from 8 bp to 20 bp (1998). Work done by Volker and colleagues monitored the activity of a 200 bp plasmid, and short internal segments were found to melt between 75° C. and 95° C. (1999). Temperature transition rates used by these research groups were usually less than 60° C./hr (<0.017° C./s). Based on this information, the temperature regulation of the LightCycler™ was modified to achieve temperatures as low as 3° C. and transition rates near 0.01° C./s.

The pre-modified LightCycler™ system is a "microvolume multisample fluorimeter with rapid temperature control" capability (Wittwer et al., 1997). The basic thermal cycling device is described in detail in U.S. Pat. Nos. 5,455,175 and 5,935,522 incorporated herein in their entirety. A device similar to the LightCycler™ is described in copending U.S. patent application Ser. No. 09/651,374, also incorporated herein.

FIG. 1 illustrates all of the basic components of a working instrument used for thermal cycling and amplification product analysis. Temperature cycling is made possible by controllable high-wattage heating coils and continuous airflow. Air surrounding the instrument is continually being drawn into the chamber by the action of a radial fan found within the chamber. Rotation of the fan pushes air from the center outward and upward until it exits the top of chamber. The outward movement of air causes a low-pressure region in the center of the chamber, which draws air across the heating coils and into the chamber. A circular airflow pattern is also established within the chamber. Reaction samples are contained within small sample holders and are subjected to the thermal environment within the chamber. The fast circulating air within the chamber increases thermal transfer into or out of individual sample holders, enabling rapid thermal cycling of the sample for such applications as PCR reactions. Monitoring of product accumulation during an amplification reaction and product analysis of the samples are made possible by rotating the samples above excitation and collection optics with a stepper motor and the incorporation of fluorescent nucleic acid dyes. A blue LED functions as the excitation source for the nucleic acid dyes and excitation and signal collection occurs along the same path (paraxial orientation).

FIG. 1 shows a LightCycler™ with two-color acquisition possibilities that employs two photo diodes to collect output signals. Two dichroics are used to achieve color separation, with cutoffs at 505 nm and 560 nm, respectively. A thermocouple placed in the chamber just inside of the sample rotational path, supplies temperature feedback to the controller. Temperature, stepper motor, fan speed, and fluorescence data acquisition are controlled using LabView-based software (National Instruments, Austin, Tex.).

The non-modified chamber is constructed mainly of anodized aluminum with 24 brass insets to hold sample-containing glass capillaries (see FIG. 1). Insulation lines all sides of the inside of the chamber (FIG. 1—insulation lining the inside of the chamber is shaded gray). Instrumentation modifications are divided into chamber modifications, and temperature control modifications. To avoid the need to redesign the standard optical pathways used for fluorescence monitoring, chamber modifications were minimized. Modifications to the standard system included, additional insulation enhancements to the inside and outside of the chamber, the utilization of a Peltier cooling/heating device, dimension adjustments to the top opening of the sample carousel, the incorporation of an additional bearing, coolant bath incorporation and a fan modification. The particular LightCycler™ modified was a standard 24-sample thermal cycler (LC24).

Chamber Modifications

Figure 2:
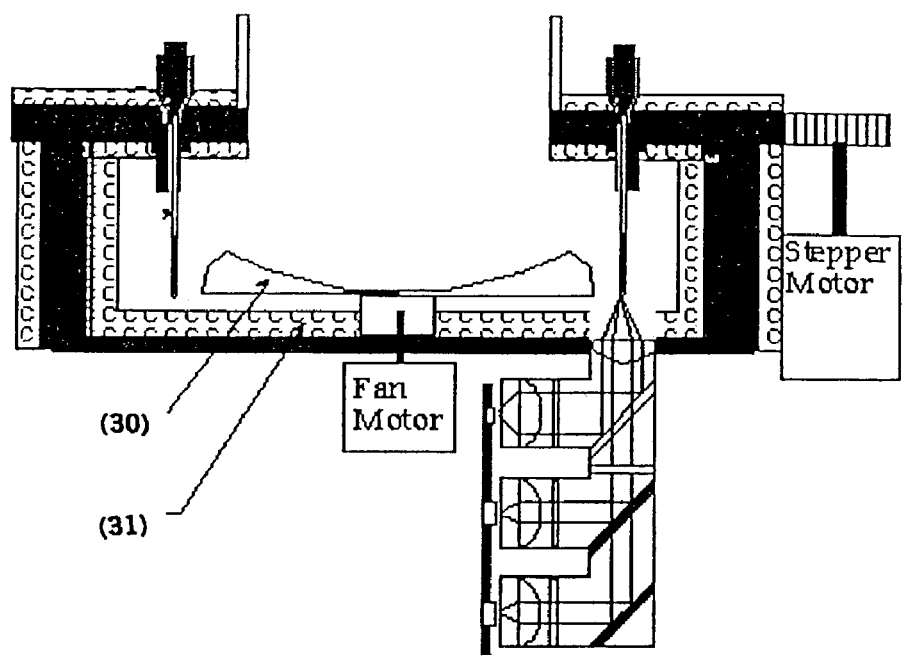
FIG. 2 is an Illustration demonstrating minor chamber modifications made to the 24 sample LightCycler. Only minor modifications were desired to maintain the integrity of the current sample positioning and fluorescent monitoring systems. The standard heating coils and air-inlet pipe were removed and the original radial chamber fan was replaced by an axial fan (30). The power to the chamber fan was decreased by half. Additional insulation (31) was added to all sections of the reaction chamber and sample carousel (slightly shaded regions) to decrease the thermal loading of the chamber.

To take full advantage of the current chamber design with fast thermal transfer rates into glass capillaries, only small modification were made to the reaction chamber. As indicated above, additional insulation was added to the inside and outside of the chamber. Most importantly, new insulation was placed on the top of the sample carousel to reduce the rapid transfer of heat into the chamber through the brass insets. Additional insulation was also attached to the sides of the sample chamber. The standard radial chamber fan was replaced with an axial fan and power to the fan motor was reduced by half. FIG. 2 illustrates the removal of the standard heating coils and other chamber adjustments.

Temperature Control Modifications

Figure 3:
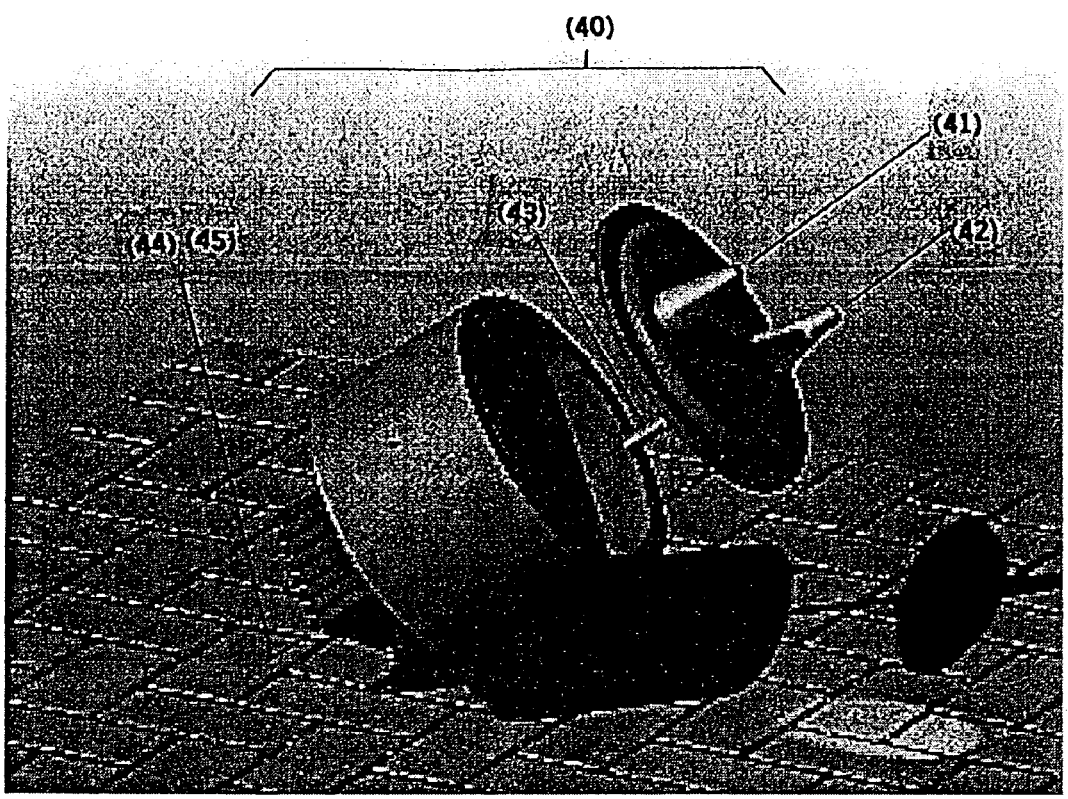
FIG. 3 is a rendering of the aluminum coolant-bath (40) used to maintain cool upper heat sink temperatures. Two brass connectors (41–42) (extending from the lid of the coolant-bath) are used to connect the rubber tubing carrying a 10% EtOH/$H_2O$ coolant. Extending down from the coolant-bath lid and reaching the bottom of the bath is a short section of rubber tubing (43) that enabled almost complete draining of the coolant-bath with the use of an external air compressor. A small hole in the rubber tubing section, just below the sight of attachment (not visible in this figure), allows air to escape upon chamber refilling. Extending from the bottom of the coolant bath are the Peltier module (44) and accompanying heat sink (45). Four screws were used to tightly secure the lower heat sink and Peltier module to the bottom of the bath. Three screws were used to seal the lid onto the chamber.

In order to minimize changes, the cooling/heating source was placed in the same location as the heating elements in the standard LightCycler™. Estimated chamber properties resulting from system modeling were used to select a Peltier cooler/heater module (Melcor Materials Electronic Products Corporation, Trenton, N.J., Part # CP 1.0-127-05L-1) based on wattage output and dimensions. Two heat sinks (Wakefield Engineering, Wakefield, Mass., Part # 698-100AB) were obtained and modified for use in conjunction with the Peltier module; one heat sink for both the hot and cold sides of the module. For optimal Peltier operation with continuous cooling of the "hot" heat sink, an aluminum water-bath or coolantbath with continuous coolant flow capabilities was also designed and machined (see FIG. 3). The upper heat sink was placed within the coolant chamber and the lower heat sink extended off of the Peltier module into the reaction chamber. The final shape of the upper heat sink placed in the coolant chamber was cylindrical with a bottom diameter of 1.75 inches (4.4 cm) and a height of 1.2 inches (3.0 cm.). The bottom heat sink was cut to the same dimension but the fins were modified to maximize heat sink penetration into the chamber and still allow for fan rotation.

Small modifications to the sample carousel were required to allow for both the incorporation of the coolant bath with accompanying heat sinks and carousel rotation while maintaining a closed system Allowing for rotation about the Peltier module was accomplished by slightly enlarging the top opening and securing a 2.5" OD (2.0" ID) mechanical bearing (Kaydon Corp., Muskegon, Mich.). The mechanical bearing allowed the aluminum coolant chamber to remain stationary while the sample carousel rotates beneath.

Peltier Module Cooling/Heating System Including Coolant-Bath

Thermal input into the sample carousel was accomplished with a 60 W (3.9 A 15 Volt) Peltier module (Melcor Corp. Part # CP 1.0-127-051-1), two modified heat sinks (mentioned above) and a custom designed/built aluminum coolant-bath. The 3 cm square Peltier module was secured to the underside of the coolant bath with four screws that extended up through both the lower heat sink and underside of the coolant bath into four 6-40 tapped holes in the upper heat sink. The configuration was such that tightening of the screws constrains the module in-between the lower heat sink and the underside of the coolant-bath. Thermal paste (Melcor Corp. Part # TCE-001) was used at every interface to enhance thermal transfer from the module to the lower heat sink and the coolant-bath. The upper heat sink was included within the coolant-bath to increase the surface area exposed to the liquid coolant. Two additional thermocouples read by a digital thermometer (Physitemp Instruments, Inc. Clifton, N.J.) were used to monitor Peltier module performance. One was placed on the lower heat sink and the other within the coolant-bath on the upper heat sink. Both thermocouples were secured to the respective heat sinks with thermal epoxy (Melcor Corp. part # TCE-001).

Figure 4:
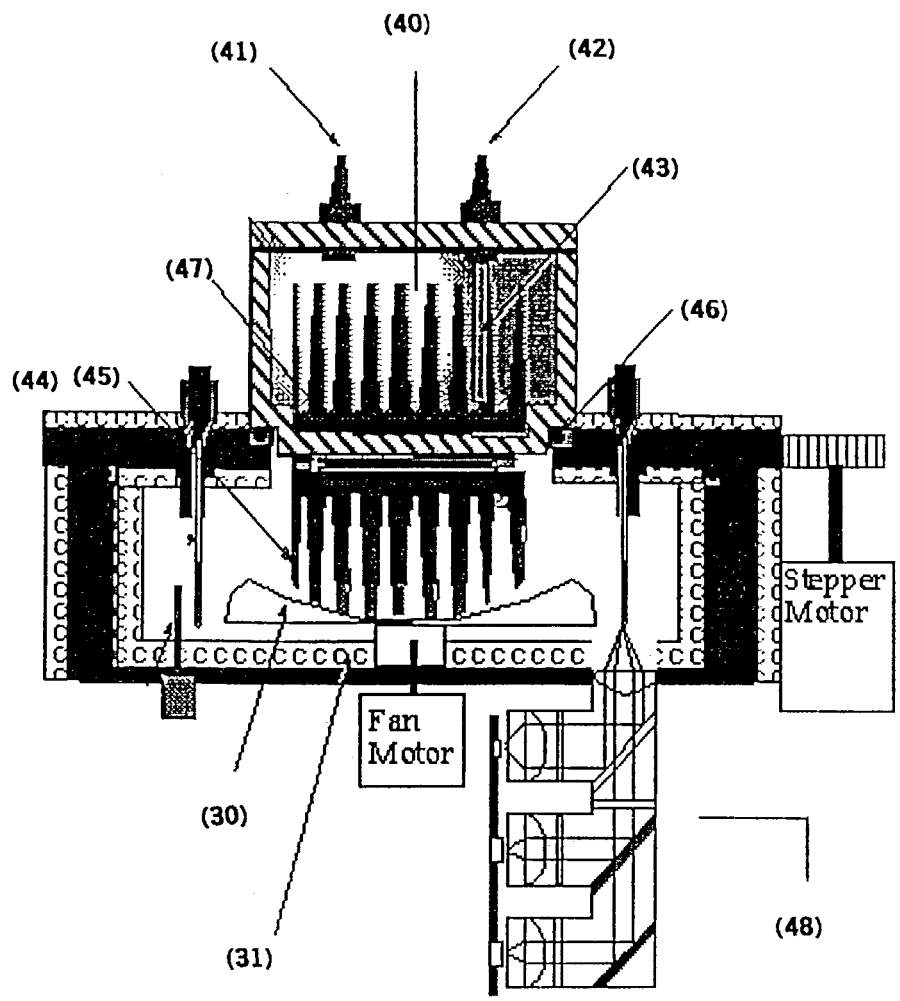
FIG. 4 is an illustration of the final organization of the modified LC24 instrument. To allow for the incorporation of the coolant-bath (40) with attached heat sinks (44) and Peltier module (45), the top opening of the sample carousel (3) was widened and a bearing (46) was added to allow for carousel rotation about the coolant-bath (40). Brass coolant intake (41) and outlet fixtures (42) are noted as well as the rubber outlet tubing (43) that extends to the bottom of the chamber (40) to enable chamber-coolant voiding. The lower heat sink (44) was machined identical to the upper heat sink (47), but required some additional alterations to allow for fan (30) rotation. Final instrument modifications create a completely closed, well insulated system allowing for freezing conditions. One externally controlled Peltier module (45) supplies both active cooling and heating input. Chamber modifications had no effect on standard fluorescent monitoring pathways (48).

The coolant bath, machined from 3 inch aluminum bar stock, consisted of a cup-like coolant bath and a lid. The lid was secured to the top of the bath with 3 half-inch (1.75 cm) 6-40 screws. A rubber gasket was placed in between the lid and the bath to make the junction watertight. The internal volume of the coolant-bath was 80 mL (without the upper heat sink). A 10% EtOH solution was used as the liquid coolant and was piped into and out of the reservoir using rubber tubing attached to two copper fixtures that were screwed into the lid. Coolant circulation was powered by a circulating thermostat (Haake, Karlsruhe, Germany, # FK16), which had refrigerating and heating capabilities. Room temperature coolant flow rates were approximately 1400 mL/min. The 10% ethanol solution depressed the freezing point of water about 10° C. (Weast, CRC Handbook of Chemistry and Physics, 63rd edition, CRC Press, Boca Raton, Fla. (1982) p. D-236); however as the coolant was cooled the solution became slightly more viscous and flow rates decreased. With coolant temperatures at −10° C. flow rates were roughly half of that at room temperature. Extending down from the lumen of one copper fixture was a segment of rubber tubing to enable automatic coolant drainage with an external air compressor. As air was forced into the sealed coolant chamber, liquid was forced out through the tube extension. Since the tube reached just above the bottom of the chamber, almost complete voiding of the coolant chamber was possible. A small hole in the rubber tubing extension, just below the copper fixture, allowed for the resulting air to escape upon chamber refilling. FIG. 4 illustrates complete coolant-bath design and incorporation into the sample reaction chamber. Heat sink designs are also illustrated in FIG. 4.

Temperature Control Modifications

Figure 5:
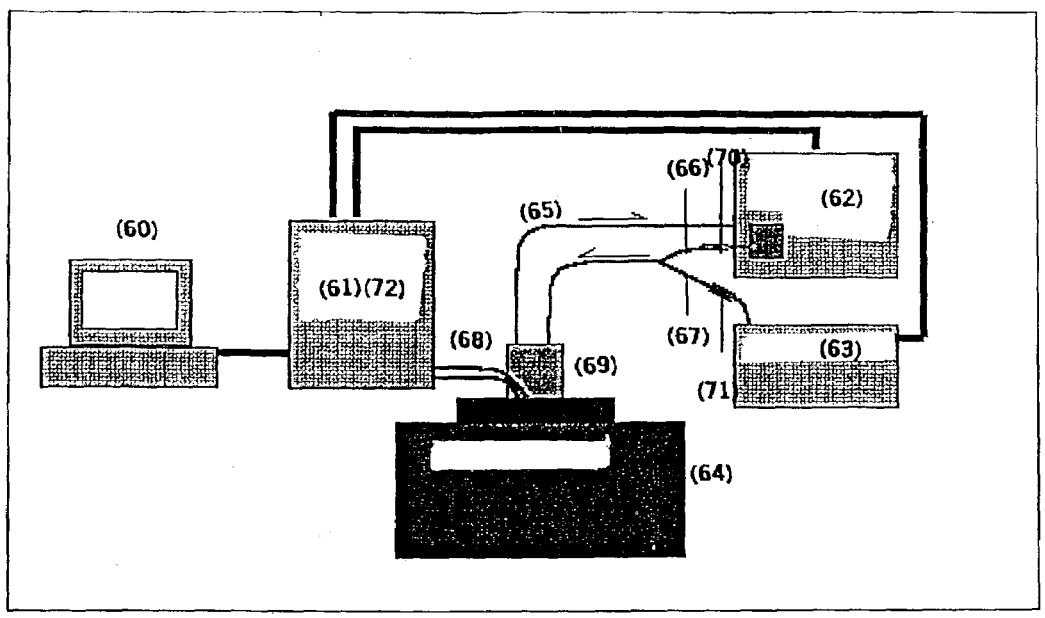
FIG. 5 is an illustration of the basic components of the external control system used to regulate reaction chamber temperatures. One computer (60), running LabView 5.1 (National Instruments), is used to control the standard LightCycler control software as well as the new, custom built control electronics. Chamber temperature feedback and control circuitries are consolidated within the Power Box (61). The black lines extending from the Power Box (61) to the pump (62) and compressor (63) represent control inputs originating from circuitry within the PowerBox (61). The two lines extending from the bottom-right of the control box (61) represent power input into the Peltier module (64). Coolant tubing (65–67) is represented by lines extending from both the pump (62) and compressor (63) into the top of the aluminum coolant-bath (68). Two one-way check valves (small gray boxes in-line with tubing extending from the compressor and pump) (69–70) were used to maintain proper air and liquid-coolant flow directions. One 100 W power supply (71), housed within the Power Box (61), supplies power to the control circuitry as well as driving power to the Peltier module (64).

The new Peltier module beating/cooling system also required a new control system, since the high-wattage pulse-width-modulated control scheme used by the LightCycler™ is incompatible with Peltier modules. Consequently, a separate power supply and linear controller were built and incorporated into the system. FIG. 5 illustrates the relationship of each component in the modified system. A computer, running LabView, was used to control all aspects of the modified system, including pump activity, compressor activity, the power output from a 100 W power supply and the standard run-software for the LightCycler™. As illustrated in FIG. 5, the Power Box acts as a jumper station that channels input and output from each component to the computer. The Power Box also houses the power supply and control electronics that mediate the activity of each component of the system. Specific control components include, a custom built linear controller to regulate power to the Peltier module and two solid-state relays (Crydom Corp., San Diego, Calif., Part # DID07) to control the activity of the compressor and coolant pump. The linear controller consists of current-polarity control and power-regulation segments. Temperature feedback occurs through the LightCycler™ standard thermocouple.

Figure 6:
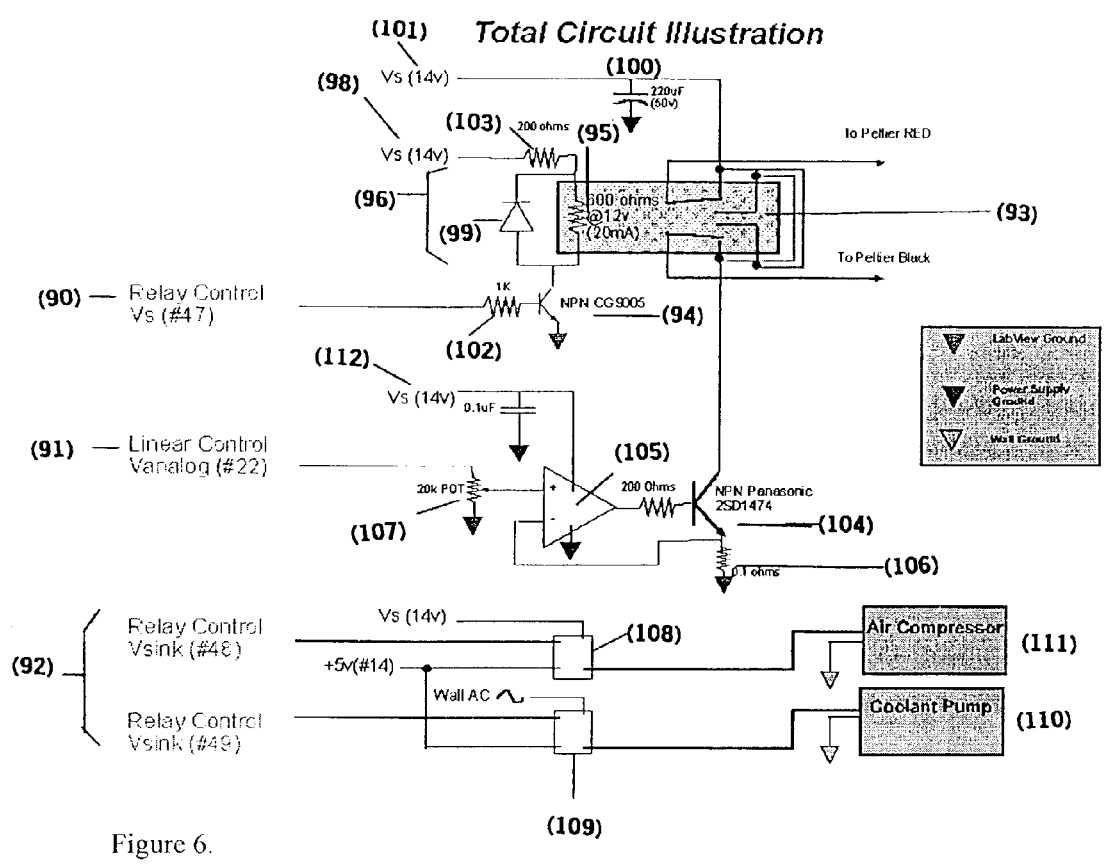
FIG. 6 depicts specific electronic components of the control circuitry used to regulate chamber temperatures. Control circuitry is divided into three sections: current polarity control through the module (90), linear power regulation to the module (91) and compressor-pump regulation (92). Polarity Control (90). Current polarity (the upper shaded region) through the Peltier module (not shown) is regulated by the state of a 12 volt 6-lead mechanical relay (93), which is controlled by the state of a low power NPN transistor (94). Lead configuration is such that coil activation reverses the current direction through the module (not shown). Relay coil (93) activation switches the relay lead configuration, and is initiated by introducing a bias on the base terminal (97) of the NPN transistor (94). The bias increases the conductance of the transistor (95) and essentially closes the circuit from the power supply (98) through the relay coil (96) to ground (99). One diode (100) is used protect the computer (101) from the small voltages generated by activating and deactivating the relay coil (96) (an inductive load). The 1 k$\Omega$ (102) and 200 $\Omega$ (103) resistors respectively, decrease power output from the computer (101) and step down the source voltage for proper transistor (95) and relay coil (96) activation. Power Regulation (91). Power regulation through the Peltier module (93) employs a high wattage NPN transistor (104) in conjunction with an operational amplifier (105) in a voltage-feedback configuration. The maximum, analog-control voltage from the computer (112) (connected to the positive terminal of the op-amp (105)) is matched to the maximum voltage drop across the 0.1 ohm resistor (106) (connected to the negative terminal of the op-amp (105)) using the 20 kΩ POT (107) (variable resistor). Connected in this manner, the operation amplifier (105) modulates the base voltage of the transistor (104) until the voltage drop across the 0.1-ohm resistor (106) matches the computer generated control voltage. Computer output, therefore modulates the power through the Peltier module (93) and ultimately chamber temperatures. Additional Control (92). Circuitry outside of the shaded regions involves the relay controls (108–109) regulating the activity of the coolant pump (110) and air compressor (111). Both relays (108-109) are wired in a "sink" configuration or use false logic. Higher wattage outputs from the computer board are possible in the sink configuration.

Specifics for each aspect of the control system are diagramed in FIG. 6. Shaded regions within FIG. 6 indicate circuits used in controlling current polarity and power-regulation through the Peltier module. The upper most shaded area of FIG. 6 shows components used to regulate current polarity through the module, and the lower shaded area represents the employed power regulation scheme.

Circuit diagrams outside of the shaded regions show control pathways for the air compressor and coolant pump. The 100 W power supply was the source voltage for all control components, except for the control voltages that were generated by LabView. A legend identifies which grounding pathways were used. Each segment of the control circuitry is discussed below.

Polarity control involves a 5 A six-pin relay, with a 12 V (20 mA) switching coil (Matsuchita Electric Works, Ltd. (Nais group), New Providence, N.J. Part # JW2SN-DC12V AJW72111), a 1 A silicon rectifier (diode) (available through Digi-Key Inc., Part # IN4007GICT-ND), a low power NPN transistor (available through Digi-Key. Part # 2Sd 1474-ND), one 1-Kohm resistor, 200 ohm resistor and one 220 mF 50 volt capacitor. The 200 ohm resistor steps down the voltage drop across the relay coil from 14 V to 10.5 V, and the 1K ohm resistor limits the current output from LabView. Since the relay control coil is an inductive load, the diode is used to protect computer circuitry from any currents resulting from coil deactivation. The wiring on the right side of the relay allows for current direction changes that correlate with coil activity and the wiring on the left side illustrates coil activation control.

The six-pin, two-state relay allows for current-direction changes through the module while maintaining a constant polarity across the relay. To illustrate, if we follow the relay's default lead configuration, as shown in FIG. 6, a positive voltage is seen by the red lead of the module and a voltage drop across the relay occurs between the red and black leads. The negative black wire coming from the Peltier module is then connected to the lead connected to the power transistor. If the lead configuration is changed by coil activation, the positive voltage is shunted to the bottom side of the relay (gray wire) where it is connected to the black lead of the module. A voltage drop then occurs across the module in the opposite polarity (direction) of the default case. The voltage returning from the Peltier module (now through the red wire) is shunted directly to the lead connected to the power transistor. In this manner the power-regulating transistor for the Peltier module will always see the same current polarity regardless of the current direction through the module.

The coil activation of the relay was controlled as follows. The amount of power allowed to pass from the source voltage pin (labeled Vs (14 v)) to the LabView ground, or the power through the control coil within the relay, was regulated by the state of NPN transistor. A 5 Vbias introduced at the transistor's gate by the digital control pin #47 increases the conductance of the transistor and allows full power to travel through the relay coil. The current passing through the coil creates a magnetic field which is used to change the internal lead configuration of the relay, which in turn changes the direction of the current through the Peltier module. Dropping the control voltage at pin #47 back to zero causes the conductance of the transistor to return to normal, the power through the control coil to stop and the relay lead configuration to return back to the normal state. Any voltage generated by the control coil upon deactivation is not allowed to enter back into the control circuitry by the action of the diode.

Peltier module power regulation involves one NPN Panasonic power-transistor (Panasonic, Secaucus, N.J. Part # 2SD1474) designed for high voltage applications, an operational amplifier (Analog Devices Inc., Norwood, Mass. Part # AD5941), one 20 k-ohm POT (variable resistor), one 200-ohm resistor, one 0.1-ohm resistor and one 0.1 mF capacitor. The system was designed to give voltage-regulated linear control over the power delivered to the Peltier module. Linear power regulation is made possible by first, accounting for the non-linear properties of the transistor with the use of an operational amplifier and second, by matching the maximum voltage seen on the positive op-amp terminal to the voltage across the 0.1-ohm resistor. If the maximum current draw of the Peltier module is assumed to be 4 A (actual maximum current is 3.9 as indicated by manufacturer) the maximum voltage drop across the 0.1-ohm resistor, following Ohm's Law, will be 0.4 V(Ohm's Law: V=IR). Since the maximum voltage output from LabView is 10 V the POT was set at the 800 and 19200-ohms position with the positive terminal of the op-amp connected to the center pin of the POT. Again following Ohm's Law, at 10 V across the POT with a total resistance of 20,000-ohm, 0.0005 amps flow through circuit. Individual voltage drops would then be 0.4 V (800 times 0.0005) and 9.6 V(192000 times 0.0005). With this configuration, as the control voltage from LabView varies between 0 and 10 V, the op-amp will vary the gate bias of the power-transistor changing its conductance in an attempt to match the incoming control voltage (from LabView) to the voltage drop across the 0.1-ohm resistor. Consequently, the power through the Peltier module is regulated by the conductance state of the transistor, which is regulated by the voltage at the positive terminal of the op-amp. A completely closed looped system is formed when chamber temperature variations resulting from Peltier activity are fed back into a LabView-based controller.

Two additional control pathways were used to control the activity of the air-compressor and coolant pump, which also affect module performance. Activation of the air-compressor drains the aluminum coolant-chamber and the pump supplies continuous coolant circulation. Draining the chamber allows the upper heat sink to increase in temperature, while coolant circulation maintains the upper heat sink very near the temperature of the coolant. Two check valves (one-way valves, United States Plastic Corp., Lima, Ohio. Part #22294) were placed immediately after both the compressor and pump to ensure the proper direction of air and fluid flow is maintained. Two additional LabView digital output pins, in a "sink" configuration, were used to switch two solid-state relays to turn on or off the compressor or water pump. One DC/AC solid-state relay (Continental Industries Inc., Mesa, Ark. #AC-DC-108-000) was used to connect the water pump with wall current, and a DC/DC (Crydom. Part # D1D07) relay was used to activate an additional relay within the control circuitry of the air-compressor (the air compressor was designed for computer control in this fashion). In the sink configuration, relays were controlled by connecting a 5 V source voltage to one terminal and the digital control voltage to the other. When the digital control voltage drops from 5 V to 0 V, a 5 V drop is present across the control terminals and the relay is activated. This configuration allows for higher wattage output from the National Instruments I/O board. (National Instruments Corp., 1995).

Determination of Instrument Performance

Performance assessment was accomplished by performing a set temperature ramp on a standard 24 sample LightCycler™ (LC24), a 32 sample LightCycler™ (LC32), and the modified LightCycler™ (modLC24) and comparing the results. The instruments were to increase the chamber temperature from 40° C. to 90° C. at a temperature transition rate of 0.1° C./s (a rate of 0.05° C./s was used for the modLC24). The recorded temperature tracings were converted into error signals and graphed to show temperature variations about the target temperature ramp. The target temperature at any time interval is represented by the line passing through starting and ending temperatures (40° and 90° C. respectively) with a slope of 0.1° C./s or 0.05° C./s. By subtracting the target temperature at any given time from the actual chamber temperature reading an error signal is generated. This error signal was plotted to demonstrate the performance of each machine. Global variations (over the entire time scale of the run), determined by calculating the difference between the maximum and minimum error readings, and local variations (small time scale, ~10 seconds), determined by local maximums and minimums, were compared to determine temperature control performance.

During the construction of the modified LC24, fan speeds for the new axial fan were optimized. Optimization was performed by inserting a POT in series with the fan motor while maintaining full power across the Peltier module and constant coolant circulation rates. The temperature of the chamber after 1 minute was recorded along with the current voltage drop across the POT. The voltage drop across the variable resistor that gave the coolest chamber temperature after one minute was recorded.

Instrument Performance Results

MatLab calculations of the equivalent circuit model with and without the fan running were made. The thermal load of the chamber was found to be 6.1 watts and 4.8 watts (with and without the fan respectively). The total thermal load calculation of the system was repeated with additional internal and external insulation (top and sides only). The additional insulation was calculated to decrease system loses, respectively, to 3.6 and 3.1 watts, with and without the fan operating.

Figure 7:
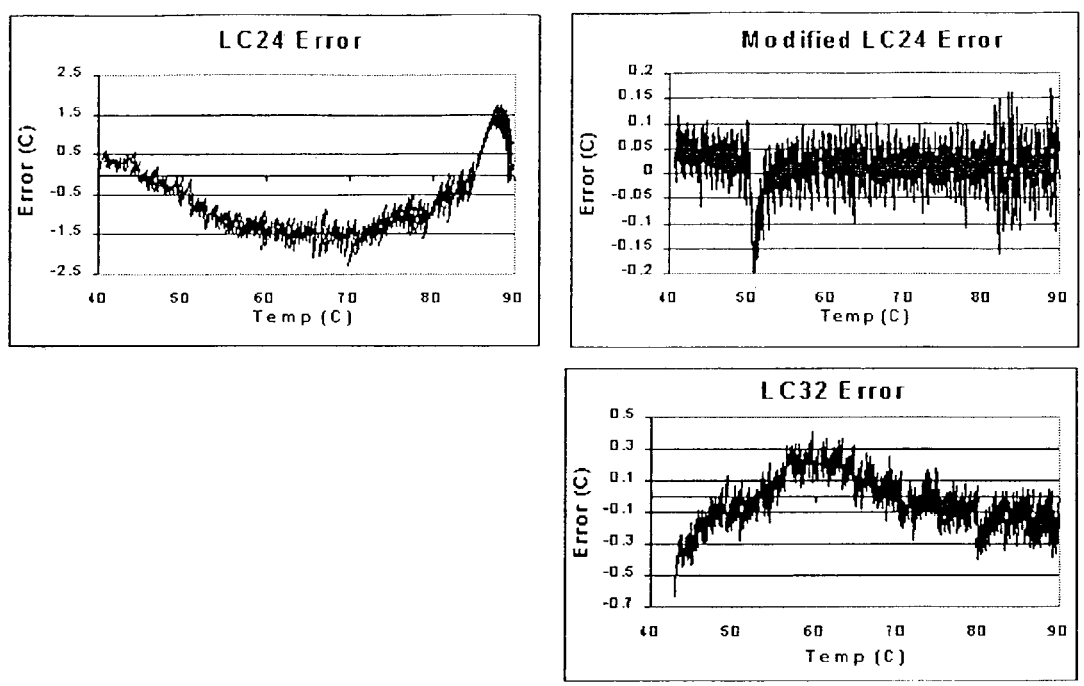
FIG. 7 depicts error versus temperature plots demonstrating the abilities of standard LC24 (a), the modified LC24 (c), and the LC32 (d) to follow a target temperature ramp from 40° C. to 90° C. Individual ramp rates were 0.05° C./s for the modified LC24 and 0.1° C./s, for LC24 and LC32. Error plots were made by subtracting the actual chamber temperature from the target temperature for any given time and then plotting the error signal against the target temperature. Between the three machines, the modified LC24 performed that best with more target-temperature centered errors. Both the LC24 and LC32 drifted substantially from the target temperature.

The accuracy and precision of the modified LC24 was found to be close to 4-times better than the standard temperature control in the LightCycler™ 24 (LC24) machine. Graphical representations of the error signals from the two machines are shown in FIG. 7. Peak to peak global and local variations are worse in the LC24 machine. The maximum recorded error of the LC24 was observed to be more than 3 degrees off from the target temperature, while the modified LC24 machined maintained a temperature within 0.2° C. of the target. More importantly, local variations (a small time scale of less than 10 seconds) in the modLC24 and the LC24 were 0.32° C. and 1.3° C., respectively. A tabulation of the observed performance of the two machines is found in Table 1. The standard deviation of the entire error signal as well as the maximum and minimum errors are indicated. Also included in Table 1 are the overall temperature ranges of the instruments and the possible ramp rates for each machine. presented in the last five columns. The second and third columns list slowest possible ramp rates and the normal working temperature range respectively, for each machine. Specific machines are identified in the left-most column. All three machines were to follow a temperature ramp from 40 C to 90 C, the respective ramp rates used for the standard LC24, the modified LC24 and the LC32 were 0.1 C/sec, 0.05 C/sec and 0.1 C/sec.

Modifications to the LC24 increased the thermal stability of the system as well as the temperature range of the instrument. The working temperature range of the standard 24 LightCycler™ was between 40° and 100° C. Active cooling by the Peltier module within the modified LC24 decreased the lower temperature range by about 40 degrees to 0° C. The upper temperature limit is 10 degrees less than the other machine. Chamber temperatures below 10° C. required coolant temperatures below zero and chamber temperatures above 80° C. required coolant temperatures above 60° C.

Temperature extremes were therefore dependent on the wattage of the Peltier module and the possible ΔT of the module. At the extremes of the temperature range and at the optimal power deliverance to the axial fan (50% of standard LC24 fan power), absolute lower heat sink temperatures always exceeded absolute chamber temperatures by at least 15° C. The maximum sustained ΔT observed across the upper and lower heat sinks, at any coolant temperature, was roughly 45° C.

Instrumentation Discussion

Converting the sample chamber into a closed system allows for a fourfold increase in temperature control performance of the modified LC24. In the standard LightCycler™ configuration, air from within the chamber is continuously forced out the top air vents by the action of the chamber fan, and new air continuously enters the chamber from the inlet pipe. Proper chamber temperature control therefore depends on properly heating incoming air as it quickly passes over the heating elements just superior to the chamber and adequate mixing of the chamber air by the chamber fan. Mixing is needed since incoming air passes quickly over the heating coils resulting in non-homogenous temperatures within the incoming air. Fast fan speeds are therefore required to adequately mix incoming air. Fast fan speeds also increase the heat transfer rates into the sample capillaries, since thermal transfer rates depend on air speed (Hagen, *Heat Transfer with Applications,* 1st edition, Prentice Hall, Upper Saddle River, N.J. (1999)). Fast temperature cycling is therefore possible and consequently many cycles of a PCR reaction can take place in a relatively short period

TABLE 1

Comparison of Instrument Performance

| Instrument | Slowest Ramp (C/sec) | Temperature Range | Peak to Peak Error (local) | Peak to Peak Error (Global) | Standard Deviation | Max. Error | Min. Error |
|---|---|---|---|---|---|---|---|
| LC24 | 0.1 | 40 to 100 | 1.3 | 4.0 | 0.84 | 1.75 | −2.25 |
| ModLC24 | 0.01 | 3 to 80 | 0.32 | 0.39 | 0.045 | 0.168 | −0.218 |
| LC32 | 0.1 | 40 to 100 | 0.48 | 1.04 | 0.165 | 0.414 | −0.63 |

Table 1. Tabulation of the instrument performance data. Time specific error data were calculated in the manner described in FIG. 7 and was used to generate the data of time. As fan speeds and airflow increase, however, the air exposure time over the control surface (heating element) decreases and greater temperature differences within the incoming air mass will exist. The heated, incoming air will be less and less homogenous, which requires more mixing and faster fan speeds. A shorter heating element exposure time also necessitates finer controller precision to make proper power adjustments on small time scales. Finding the optimum control scheme for fast fan speeds has received much attention from the makers of the LightCycler™. It should also be noted that the LightCycler™ line of instruments was specifically designed for rapid temperature cycling and not slow temperature transitions.

By closing the system, and not continuously introducing new air into the sample chamber, a homogenous environment can be maintained within the sample chamber using a low-power heater/cooler element and slower fan speeds. Closure of the system yields tighter temperature regulation by increasing the mixing time and by increasing the time of exposure of the air to the control surface (lower heat sink). The increase in mixing time causes the chamber to react to changes in control surface temperatures more like one thermal mass rather than a collection of very small volumes of air. The chamber air behaves like one mass and responds slowly to temperature changes on the control surface. The system then can only respond slowly and slower rates and better thermal stability become characteristics of the system.

Chamber reaction temperatures ranging from 0° to 90° C. are made possible because of the Peltier module and slower fan speeds. Active cooling and heating are enabled by changing the polarity across the Peltier module using the described control scheme. By decreasing the fan speed the thermal loss of the system through the walls of the chamber is reduced, allowing for a low-wattage temperature regulation scheme to still achieve the desired chamber conditions. The higher fan speeds in the LC24 increase not only the thermal transfer rates from the heating elements to the air but also the thermal transfer rates through the walls of the chamber.

Measured temperatures of individual system components, such as the maximum $\Delta T$ sustained across the two heat sinks, and the temperature difference between the lower heat sink and the chamber temperatures, give insights into the actual thermal properties of the system. The observed 15° C. difference between the lower heat sink temperature and the chamber temperature at maximum power output, represents the balance between the thermal transfer from the control surface (lower heat sink) and that through the walls of the chamber. The observed $\Delta T$ of 45° C. across the two heat sinks depends on the Peltier module wattage, the thermal transfer rates from the upper heat sink to the liquid coolant and the thermal loading through the walls of the aluminum coolant-bath.

If desired, an increase in temperature range could be accomplished by changing a couple aspects of the current system. Temperature range enhancements could be accomplished by increasing Peltier module characteristics (size, wattage, $\Delta T$), by decreasing thermal transfer through chamber walls and increasing thermal transfer from control surfaces (lower and upper heat sinks). The additional insulation added to the chamber was an attempt to decrease thermal transfer through the walls of the chamber. It might be possible to increase the insulation to the point where increasing the airflow within the chamber (faster fan speeds) will have more of an affect on thermal transfer rates from the control surface than through the chamber walls. More directed air flow across the lower heat sink could also increase the thermal transfer into the chamber from the heat sink while not greatly increasing the air flow along the walls of the chamber. The change from a radial fan to an axial fan attempted to increase airflow across the lower heat sink.

Increasing the coolant flow rates could also improve Peltier module performance by increasing the thermal transfer from the upper heat sink. Faster flow rates within the coolant bath would have the same system effects as increasing the airflow within the sample chamber; thermal transfer rates from the upper heat sink into the coolant would increase. Better upper heat sink to coolant transfer rates would increase the performance of the Peltier module by increasing the possible $\Delta T$ across the two heat sinks as upper heat sink temperatures would be closer to coolant temperatures. The thermal transfer rate through the walls of the coolantbath would also increase however, which would tend to decrease the performance of the module. Insulation was therefore also placed on the outside of the coolant bath.

Example 2

Secondary Structure Melting Curves and Demonstration of Multiple Domain Melting

A model oligonucleotide system was designed to (1) demonstrate secondary structure melting curves by monitoring fluorescence intensity of the double strand DNA specific nucleic acid dye SYBR Green I, (2) empirically determine secondary structure melting temperature ranges, (3) demonstrate multiple domain melting using SYBR Green I fluorescence and, (4) demonstrate sequence specific melting of secondary structures using SYBR Green I. Multiple domain melting of nucleic acids has previously been reported using differential scanning calorimetry (Kulinski, 1991; Paner et al., 1990), using optical absorbance (Volker et al., 1999) and by the monitoring of covalently bound fluorophores (Vamosi and Clegg, 1998; Volker et al., 1999), but multiple domain melting determinations have not been shown using double stranded nucleic acid-specific dyes such as SYBR Green I.

Model Oligonucleotide Design

Figure 9:
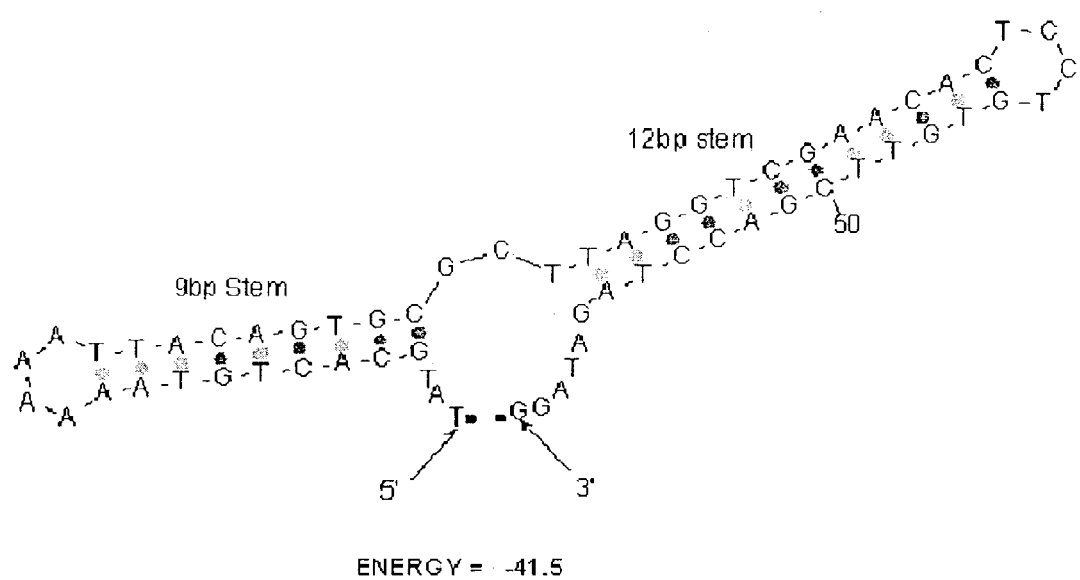
FIG. 9 depicts the secondary structure of the two hairpin containing model oligo (9–12 hairpin) (SEQ ID NO:1) as calculated by Mfold software. The 5' and 3' ends are indicated as well as stem lengths. The Mfold software, available online at www.mfold.bumet.edu.au/ma_form, predicts secondary structure by using nearest neighbor calculations (SantaLucia, 1998). The free energy calculation of the given structure at 20° C. is given just below the illustration

Thirteen specifically designed model nucleic acid oligonucleotides (SEQ ID NOS:1–3) were synthesized on a Perceptive BioSystems 8909 MOSS synthesizer (Framingham, Mass.) using standard fast expidite phosphoramidite chemistry by IT Biochem (Salt Lake City, Utah). Post synthesis, each oligonucleotide was purified using $C_{18}$ reverse-phase HPLC with standard deprotecting and desalting conditions. Each of the thirteen oligonucleotides contained at least one hairpin with four nucleotides in the loop and stem lengths varying from 3 base pairs (bp) to 18 bp (see FIG. 8). Loop sequences for stem lengths of nine base pairs and shorter were all the same (-AAAA-). Loop sequences for stem lengths greater than nine were all-TCCT-. An effort was made to maintain consistent GC content in all of the stems, but stem sequences are not completely identical. The average GC content of all of the oligonucleotides is about 48%. FIG. 8 shows the specific sequences for each oligonucleotide and their proposed secondary structure. From the thirteen sequences, two oligonucleotides contain mismatches within the stem sequence, two have additional bases not incorporated within the secondary structure (tails) and one contains multiple hairpins with differing stem lengths (9 bp and 12 bp). Following synthesis, all oligonucleotides were re-suspended in 1×TE' (1:100 dilution of 1M TRIS-HCL with 0.01M EDTA) and 260/280 ratios were taken using an Ultraspec 2000 spectrophotometer (Pharmacia Biotech, Cambridge, England). Since the sequences were known, nucleic acid concentrations were determined by first calculating the extinction coefficient for each oligonucleotide using published optical properties of nucleic acids (Borer, "Nucleic Acids", In *Handbook of Biochemistry and Molecular Biology*, 3rd Edition, (Fasman, ed.) CRC Press, Boca Raton, Fla. (1975) p. 589) and custom built software (CTWTool-2-18-00, Carl T. Wittwer, University of Utah, SLC, UT). Secondary structure conformations were confirmed using two nucleotide structure-prediction software packages at 20° C. and 1M NaCl, Primer Designer (Sci-ed Software, Durham, N.C.) and Mfold (Dr. M. Zuker, Washington University Medical School, St. Louis, Mo.). Primer Designer was unable to identify two hairpin structures that Mfold did. FIG. 9 shows the resulting structure of the oligonucleotide (SEQ ID NO:1) containing two hairpins as calculated by Mfold.

Assay Optimization

In anticipation of future post-PCR reaction conditions, each reaction contained DNA and SYBR Green I within a PCR buffer (IT Biochem: 50 mM "clear" buffer). Optimization runs for each of the three components were performed. First, a range of SYBR Green I and DNA concentrations was investigated followed by a range of buffer concentrations. Both the presence of melting peaks and the relative signal to noise ratio of the peak (or the standard deviation of the peak) were used as the criteria for determining optimum concentrations. The standard deviations of the observed melting peaks were calculated using standard LightCycler™ data analysis software (LCDA 3.0, Idaho Technology Inc, SLC, UT).

Initial optimization runs were performed on the oligonucleotide containing two hairpins using a LightCycler™ with 32 sample holders to speed up the optimization process. Final concentrations of SYBR Green I, DNA and buffer, optimized for viewing multiple-domain melting, were 1:20,000 stock dilution of SYBR Green I (Molecular Probes, Eugene, Oreg., Part # S-7567), 0.1 mM of DNA, and 1:50 stock dilution of the 50 mM clear PCR buffer (final component concentrations: 5 mM Tris, 5 mg/ml BSA, and 1.0 mM $Mg^{2+}$). For samples containing stems shorter than 9 bp the final DNA concentrations were changed from 1.0 mM to 3.5 mM to increase the stem-loop fluorescence. Following assay optimization, 12 of the 13 model oligonucleotides (run in repeats of six) were subjected to a 0.05° C./s temperature ramp using the modified LC24 with temperature ranges targeted around the melting transition temperatures for each oligonucleotide. The LC32 was used to collect data from the Qligonucleotide containing two hairpins. Resulting data were analyzed using standard LightCycler™ analysis software (LCDA 3.0) and $T_m$ values were tabulated. Basic statistical analysis of the $T_m$ values including mean and standard deviation calculations was also performed.

Model Oligo System Results

Results from each of the 13 oligo nucleotides including average $T_m$, standard deviations, and delta $T_m$ values ($T_m$ shifts due to stem sequence variations or oligonucleotide design differences) are found in Table 2. Specific oligonucleotides and stem sizes are identified in the two left columns. The values in the $T_m$ 1 column are mean $T_m$ values with the n for each oligo indicated on the right. The standard deviations for the melting temperatures are indicated under StDev. The oligo containing two hairpins has data for both hairpins. All data was obtained using the modified LC24 except for the 9–12 hairpin, which was obtained on the LC32.

TABLE 2

Tabulation of Model Oligo Results and Statistics

| Oligo Name | Stem Size (1) (base pairs) | Tm (1) (° C.) | StDev (1) (° C.) | Stem Size (2) (base pairs) | Tm (2) (° C.) | StDev (2) (° C.) | N |
|---|---|---|---|---|---|---|---|
| 18 Hairpin | 18 | 77.8 | 0.3 | | | | 6 |
| 15 Hairpin | 15 | 76.2 | 0.3 | | | | 4 |
| 9–12 Hairpin | 9 | 69.2 | 1.5 | 12 | 78.6 | 0.6 | 7 |
| 12 Tail | 12 tail* | 74.3 | 1.9 | | | | 4 |
| 12 Hairpin | 12 | 76.6 | 0.8 | | | | 6 |
| 12 Mismatch | 12 m** | 62.6 | 0.5 | | | | 5 |
| 9 Tail | 9 tail* | 52.7 | 1.1 | | | | 4 |
| 9 Hairpin | 9 | 60.8 | 0.5 | | | | 6 |
| 9 Mismatch | 9 m** | 45.9 | 0.5 | | | | 6 |
| 6 Hairpin | 6 | 57.7 | 1.7 | | | | 6 |
| 5 Hairpin | 5 | 49.9 | 0.7 | | | | 6 |
| 4 Hairpin | 4 | 32.9 | 0.7 | | | | 6 |
| 3 Hairpin | 3 | 17.7 | 1.8 | | | | 12 |

*indicates the presence of a 37 bp tail.
**indicates the presence of one mismatch within the hairpin stem.

Table 2. Tabulation of the results from the model oligo system. Specific oligo nucleotides and stem sizes are identified in the two left columns. The values in the $T_m$ 1 column are mean $T_m$ values with the n for each oligo indicated on the right. The standard deviations for the melting temperatures are indicated under StDev. The oligo containing two hairpins has data for both hairpins. All data was obtained using the modified LC24 except for the 9–12 hairpin, which was obtained on the LC32

Figure 10:
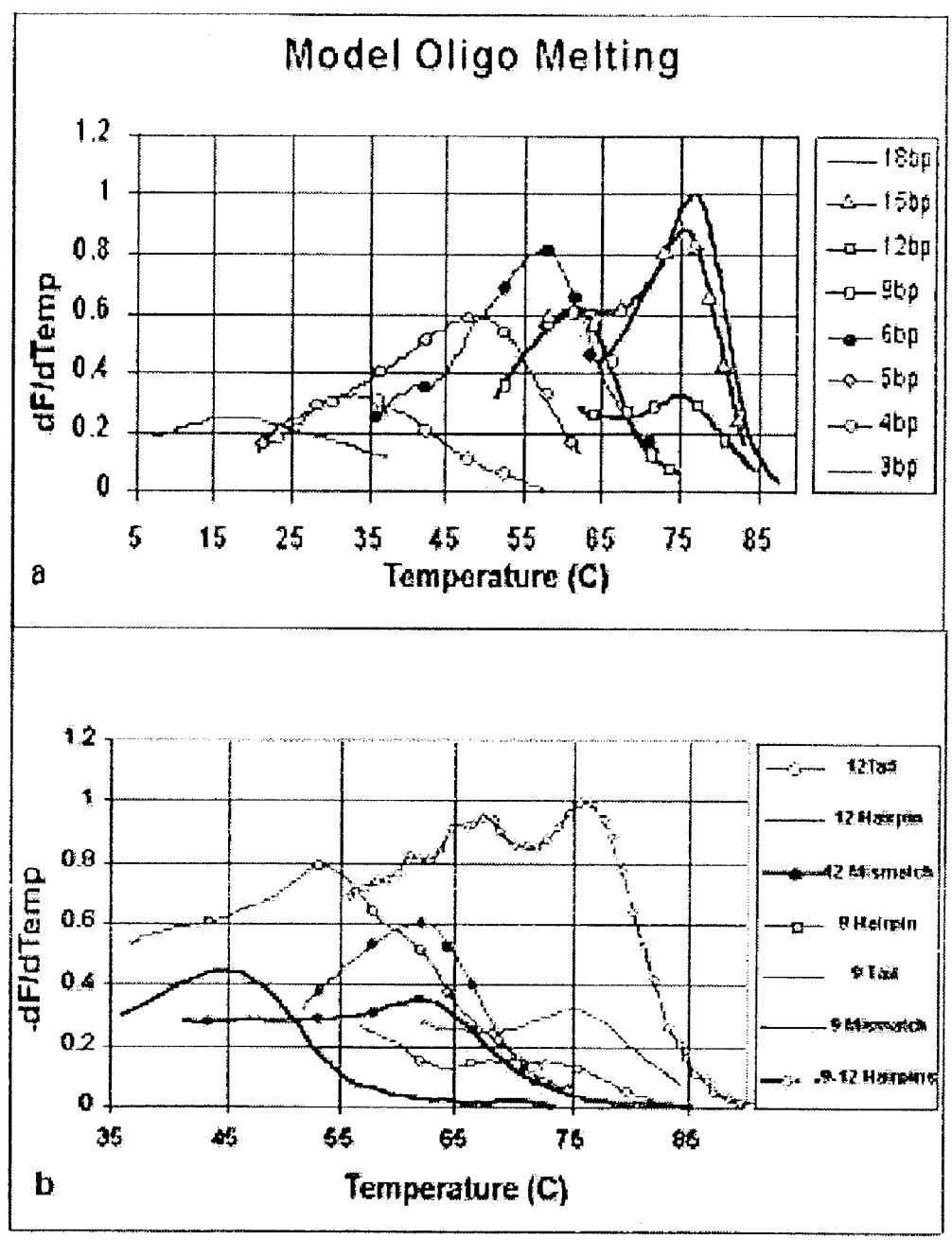
FIG. 10 depicts a compilation of representative melting curves for each of the 13 model oligonucleotides. In this figure the negative derivative of the fluorescence is plotted against temperature. Curves are fragmented since instrument melting temperature ranges were minimized to highlight the melting transitions of each sequence. All data points collected for each of the oligo nucleotides are included. Melting peaks range from 17.7° C. to 78.6° C. Typical meltingcurves for oligo nucleotides not including mismatches, tails or multiple domains are given in the upper plot (a). Curves generated from oligo nucleotides with mismatches, tails and the oligo with two hairpins are given in the lower plot (b). A $T_m$ shift to lower temperatures is evident for hairpins possessing tails or mismatches. Stabilization of the 9 bp and 12 bp hairpins in the double hairpin oligo (9–12 Hairpin) is shown in the lower plot.

Melting peak values range from 17.7° to 78° C. with $T_m$ values increasing with stem size (see FIG. 10). Variations in stem sequence and sequence length consistently gave different $T_m$ values. A compilation of melting curves for each of the 13 oligonucleotides is found in FIGS. 10*a* and 10*b*. FIG. 10*a* gives typical melting curves for oligonucleotides not including mismatches, tails or multiple domains. Melting curves for oligonucleotides containing mismatches, tails and multiple domains are shown in FIG. 10*b*. Curves corresponding to specific oligonucleotides are indicated in the legends. Melting peak height above background generally increases with hairpin stem length (see FIG. 10*a*). Peak heights for the synthesized oligonucleotides containing 12 bp hairpin stems, however were not very prominent and were similar to oligonucleotides containing hairpins with 3 bp or 4 bp stems.

Figure 11:
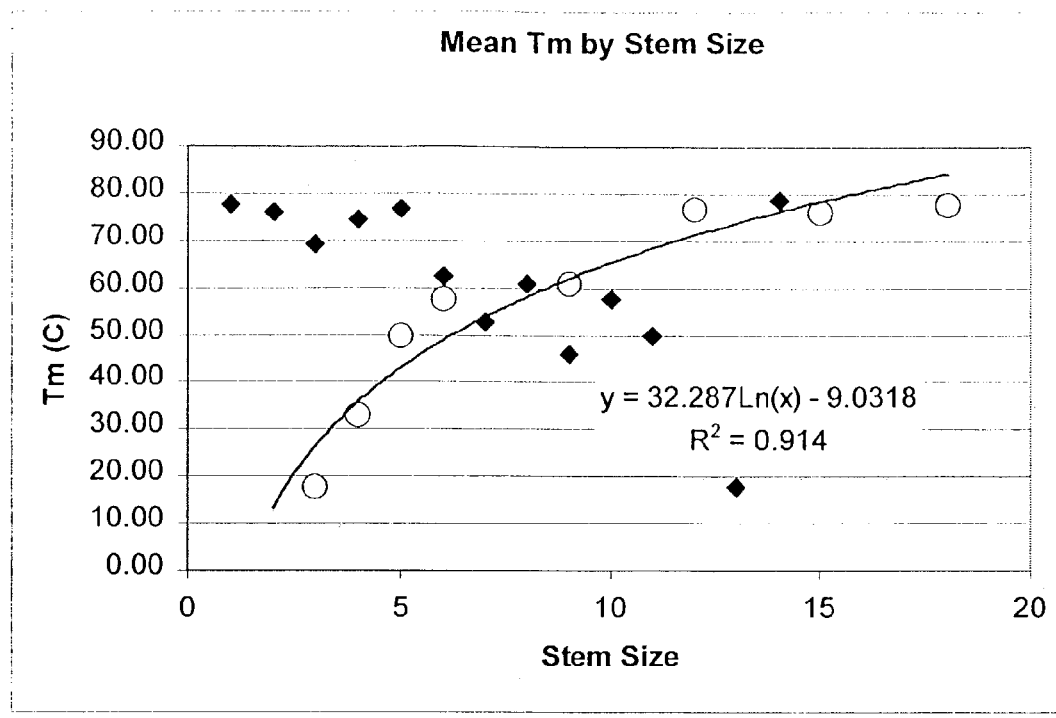
FIG. 11 shows a consolidation of mean $T_m$ values for each sequence of the model nucleic acid system by stem size. Multiple populations are found with stem sizes possessing sequence variations, such as tails, mismatches and multiple melting domains. The data from the 9–12 Hairpin is therefore included with the component stem size data (stem sizes 9 and 12). Mean $T_m$ values not including tails, mismatches or multiple stems are identified with circles and where used to calculate the logarithmic relationship between $T_m$ and stems size.

Mean $T_m$ values for each oligonucleotide were plotted against stem size to better visualize the relationship of stem size to $T_m$ (FIG. 11). The relationship between stem size and product $T_m$, excluding oligonucleotides with mismatches, tails or double stems, was best described ($R^2=0.914$) by the logarithmic relationship $$y=32.287 \ln(x)-9.0318$$

where y represents product $T_m$ in ° C., and x is stem size in base pairs (bp). The bestfit logarithmic equation was determined by least squares calculations performed by Microsoft's Excel. FIG. 11 illustrates the relationship between product $T_m$ and stem size including the calculated trend-line and $R^2$ value.

The 12 bp stem and the 15 bp stem did not melt in the expected manner as predicted by the logarithmic relationship given above. The 12 bp hairpin melted 0.4° C. higher (mean $T_m$ value) than the 15 bp stem. Standard deviations for 12 bp and 15 bp hairpins were 0.78° C. and 0.3° C., respectively. Four populations of $T_m$ values at the 9 bp and 12 bp sizes were observed. Two melting peaks were observed from the oligonucleotide containing multiple hairpins with stem sizes of 9 bp and 12 bp. The melting peak corresponding to the 9 bp was shifted +8.4° C. (plus or minus 1.5° C.) as compared to 9 bp hairpin melting alone. The melting peak corresponding to the 12 bp, in the multiple hairpin oligonucleotide, demonstrated a +2° C. $T_m$ shift (plus or minus 0.6° C.). Mismatches in the 9 bp stem and 12 bp stem gave $T_m$ shifts of −14° C. and −15° C. respectively. The presence of "tails", 37 bases not involved in stem structure, extending off of a 9 bp stem and 12 bp stem gave $T_m$ shifts of −8.1° C. and −2.2° C., respectively.

Model Oligo System Discussion

The model system was designed to accomplish each of the goals listed below.
1. Demonstrate secondary structure melting curves by monitoring fluorescence activity of a double stranded specific nucleic acid dye.
2. Empirically determine secondary structure melting temperature ranges.
3. Demonstrate multiple domain melting using double stranded specific nucleic acid dye fluorescence.
4. Demonstrate sequence specific melting of secondary structures.

Each one of these goals can be addressed using results obtained from the model system.

Results from the model oligonucleotide system demonstrate that secondary structures existing within one DNA molecule can be detectable by monitoring double stranded-specific nucleic acid dye fluorescence. A temperature range of 60° C. was also determined (between 18° and 78° C.) over which hairpins ranging in stem lengths of 3 bp to 18 bp melted. $T_m$ values varied in a sequence specific manner, as made evident by the observed $T_m$ shifts for oligonucleotides containing mismatches or tails. Finally, melting of the synthesized oligonucleotide containing two hairpin domains yielded two melting peaks, thus demonstrating multiple domain melting using double stranded-specific nucleic acid dye fluorescence. These results demonstrating sequence dependence of product $T_m$, as well as the dependence of $T_m$ on stem size, are consistent with previously published results on the sequence dependence of $T_m$ (Kulinski et al. 1991; Paner et al., 1990; Ririe et al., 1997; Vamosi and Clegg, 1998).

The ability to distinguish product length by $T_m$ decreases with an increase in stem size. As noted in FIG. 11, the slope of the curve describing the relationship between product $T_m$ and stem size flattens as stem size increases. Apparently, as stem lengths increase, additional base pairs added to the hairpin stem do not greatly increase the stability of the hairpin. However, whether or not the relationship reaches a maximum or continues upward can not be determined from these results.

A review of other nucleic acid systems and research indicates $T_m$ varies with stem length even at long duplex lengths. For example, PCR products of differing lengths can be distinguished by $T_m$ analysis using SYBR Green (Ririe et al., 1997), which suggests that increasing the stem size will continue to increase the $T_m$. However, this work was done on double stranded amplicon and the product $T_m$ values therefore represent the melting of two separate, yet complimentary, DNA strands. Within the model hairpin system, double stranded interactions are intramolecular, as opposed to intermolecular. The two complimentary segments in a hairpin don't have to "look too far" to find the complimentary strand and the concentrations of the two complementary strands are effectively increased. For example, Vamosi and Clegg observed that a 34 bp intermolecular interaction (i.e., between two separate DNA strands) melted at a lower temperature than a 20 bp intramolecular (hairpin) interaction (1998). In other words, results from an intermolecular system (e.g. work by Ririe et al., 1997) may not be directly applied to an intramolecular system. The best way then to determine the relationship between stem size and $T_m$ for intramolecular systems is to analyze hairpins with stems of increasing size or use data obtained from other intramolecular nucleic acid studies.

A good correlation between stem size and $T_m$ is shown in the present study. The validity of the correlation is indicated in part by the $R^2$ value and also by the standard deviations of the $T_m$ values recorded. The calculated relationship between stem size and $T_m$ offers a method to estimate the $T_m$ values of other hairpins.

Using the higher resolution LC32, the model oligonucleotide containing both a 9 bp and 12 bp hairpin yielded two melting peaks and demonstrated multiple-domain melting by SYBR Green I analysis (see FIG. 12b). The presence of multiple hairpins within the same molecule influenced the overall stability of the molecule as indicated by a shift in the $T_m$ of the 9 bp and 12 bp hairpins. One would assume that the 9 bp hairpin, once melted, would act similar to a tail segment and reduce the stability of the 12 bp hairpin, but instead a +2.0° C. $T_m$ shift was observed. The observed stability of the 9 bp hairpin was increased with a $T_m$ shift of +8.4° C. The reason for this stabilization is uncertain. One explanation could be that less thermal motion is present in a duplexed region of DNA as compared to a single stranded segment. As shown in FIG. 9, when both the 9 bp and 12 bp segments are in a duplex conformation, there is only a short 3 bp linker and two short 3 bp tails that are not duplexed.

Consequently, the 12 bp hairpin might stabilize the 9 bp hairpin by minimizing the thermal motion of the complete structure causing the 9 bp segment to melt at higher temperatures. Following this same logic, as the 9 bp fragment melts and becomes single stranded thereby increasing the thermal motion of the molecule, the stability of the 12 bp hairpin should decrease and a lower $T_m$ should be observed.

Concerning the effect that tails might have on a system, work done by Doktycz et al. in 1990 (*Biopolymers* 30:829–845) is relevant. Using differential scanning calorimetry, 4 bp dangling ends (or tails) of various sequences consistently melted at higher temperatures than a blunt-ended (no dangling-end) hairpin of the same sequence. Even though they observed higher $T_m$ values for dangling-end hairpins, this $T_m$ shift is attributed to a change in the type of melting transition of a hairpin with a dangling end. They argue that the presence of a dangling end causes the hairpin to melt in a complete "all or none" fashion (i.e. completely duplexed or completely single-stranded) and that blunt ended hairpins deviate from the "all or none" model (Doktycz et al., 1990). A lower temperature transition is therefore observed in the blunt ended oligonucleotide because it passes through a less stable conformation(s) as it melts. More thermal energy or enthalpy was actually needed to cause the double stranded to single stranded transition in hairpins with dangling ends (Doktycz et al., 1990). The presence of 3 bp tails in the double hairpin model oligonucleotide might also then contribute to higher thermal stabilities observed in the two hairpins.

An apparent discrepancy between the work of Doktycz and the observations from the model system described in the present example exists since all hairpins with tails in the model system experienced substantial $T_m$ decreases rather than $T_m$ increases. This discrepancy needs to be approached carefully. Doktycz used dangling ends (or tails) of four bases while the dangling ends in the model system (the 12-tail and 9-tail oligonucleotides) were 37 bases long. The degree of hairpin stabilization in the Doktycz system was closely correlated to the first base of the dangling end (Doktycz et al., 1990). With a 37 base dangling end in the model oligonucleotide system, one could reason that any stabilizing effects of the first base will be masked by the overall energy of the long non-duplexed sequence. The stabilization observed in the double hairpin model oligonucleotide, however, is supported by the conclusions made by Doktycz, since 3 bp tails are present on both the 9 bp and 12 bp hairpins. The hairpin destabilizing effect of the long tails in the model system is assumed to be entropically driven, which is supported by the work of Doktycz and others (Doktycz et al., 1990; Paner et al., 1990; Rentzeperis et al., *Nucleic Acids Res.* 21(11):2683–2689 (1993)).

Notwithstanding the relatively small range of stem lengths studied here, the stem lengths used closely approximate naturally occurring stem lengths. Nucleic acid secondary structure interactions found within small and large ribosomal subunits are composed largely of hairpins with stems sizes between 3 bp and 25 bp. (Szymanski et al., 1997; Specht et al., 1997; De Rijk et al., 1992; Kulinski, 1991). Sequences derived from natural systems consequently should be observable by $T_m$ analysis using double stranded nucleic acid-specific dyes.

Despite the uncertainty of the exact mechanics of the multiple-domain melting process, multiple domain melting using a double stranded nucleic acid-specific dye has now been confirmed in a model nucleic acid system. Furthermore, the chemical concentrations used are feasible for post PCR applications. Future work in single stranded conformational $T_m$ analysis by SYBR Green I depends on finding amplifiable regions containing sufficient, organism dependent, secondary structure differences that can be observed by $T_m$ analysis.

Example 3

Demonstration of Multiple-Component Melting of 5S rRNA

The ability to distinguish multiple melting components of 5S rRNA was shown using commercially available rRNA. *E. Coli* MRE600 5S rRNA was obtained from Roche Molecular Diagnostics (Boehringer Mannheim, GmbH, Germany, Part #206911). The 5S rRNA sample was selected to demonstrate the possibility of identifying multiple-domain melting of a natural system using SYBR Green I. Concentration optimization was performed in the same manner as the model oligonucleotide system. Final optimized concentrations were 1.0 mM RNA and a 1:15,000 stock dilution of SYBR Green in a 1.0 mM $Mg^{+2}$ PCR buffer (5 mM Tris, 5 mg/ml BSA, and 1.0 mM $Mg^{2+}$).(IT Biochem, SLC, UT).

After optimization, 5S rRNA samples were melted eight times. Melting transition rates were 0.05° C./s with starting and ending temperatures of 60° C. and 97° C., respectively. Melting curves were then analyzed using LCDA 3.0 (melting peaks were viewed using a polynomial fitting scheme with degrees to average set at 2.5° C.). Component $T_m$ values were identified by hand from software-generated plots of −dF/dT versus temperature and tabulated in Excel for statistical review.

Melting 5S rRNA with SYBR® Green I Monitoring

Figure 12:
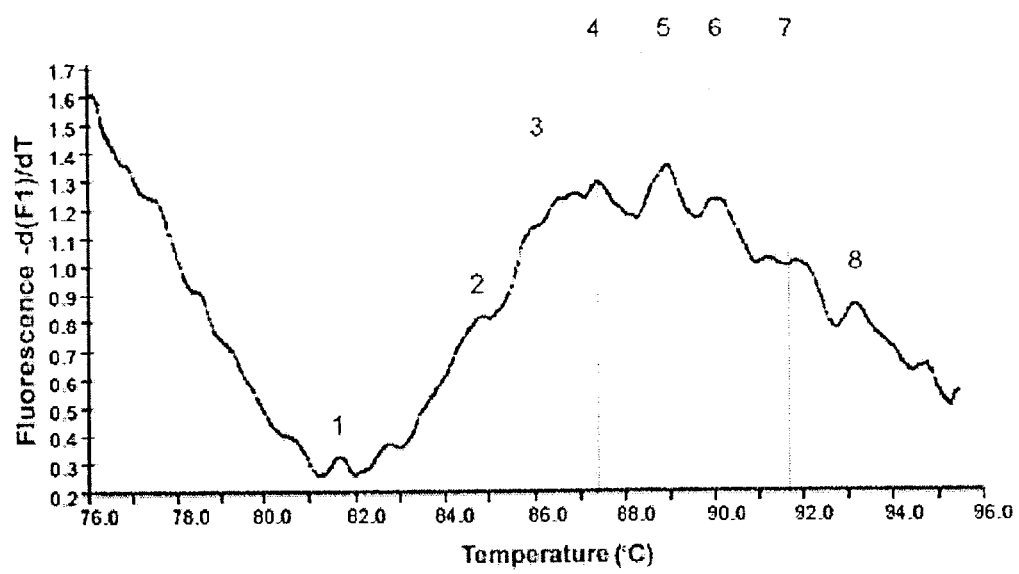
FIG. 12 depicts a representative melting profile of isolated 5S rRNA observed by SYBR Green I fluorescence. Melting data was collected by subjecting the 5S rRNA sample to a 0.05° C./s temperature ramp, from 70 to 96° C., in the presence of SYBR® Green 1 and monitoring fluorescence. In the figure the negative derivative of fluorescence is plotted against temperature. Eight melting profile components are identified. Repeat testing (n=8) gave similar results with peaks numbered 2, 5 and 6 demonstrating the most variation. Concentrations used were 1.0 mM RNA, 1:15,000 stock dilution of SYBR, and 11.0 mM $Mg^{+2}$ buffer.

FIG. 12 shows results obtained by subjecting the 5S rRNA sample, in the presence of SYBR Green I, to a 0.05° C./s temperature ramp. Duplicate runs (n=8) suggest that eight characteristics of the melting profile are repeatable. The melting profile consists of a low fluorescence (−dF/dT) "trough" between 81° C. and 82° C., and a broad melting transition containing several distinct melting components spanning a temperature range of 82° C. to 95° C. Within the low fluorescence "trough" a small peak was generally present with a mean $T_m$ of 81.7° C. No consistent melting transitions were observed below the fluorescent trough. Corresponding $T_m$ values for each run are tabulated in Table 3. In one case two of the eight-peaks were not identified. Peaks 2, 5 and 6 showed the most variation. The mean $T_m$ values and standard deviations for each peak are included. Peak five showed the highest variation in $T_m$ values with a standard deviation of 0.67° C. The mean $\Delta T_m$ values, or the temperature difference between one peak and the following peak, were 3.1°, 1.1°, 1.3°, 1.2°, 1.2°, 1.5°, and 1.4° C.

TABLE 3

Tabulation of 5s rRNA Results and Statistics

| Run Number | Peak Number | | | | | | | |
|---|---|---|---|---|---|---|---|---|
| | 1 | 2 | 3 | 4 | 5 | 6 | 7 | 8 |
| 1 | 61.1 | 84.7 | 86.2 | 88.1 | 89.4 | 90.6 | 91.7 | 93.1 |
| 2 | 81.8 | 84.8 | 86.0 | 87.0 | 88.5 | 89.5 | 91.1 | 92.7 |
| 3 | 81.7 | 83.9 | 85.0 | 85.6 | 87.2 | 89.1 | 90.7 | 92.3 |
| 4 | 81.3 | 85.0 | 85.9 | 86.8 | 89.2 | 90.4 | 92.1 | 93.4 |
| 5 | 61.7 | 85.5 | 86.6 | 87.7 | 88.9 | 90.4 | 91.6 | 93.5 |
| 6 | 81.3 | 84.2 | 86.4 | 87.5 | 88.6 | 90.4 | 91.6 | 92.6 |
| 7 | 81.7 | 84.9 | 85.5 | 87.3 | 88.9 | 90.1 | 91.6 | 92.8 |
| 8 | 82.0 | 83.5 | 86.2 | 87.7 | 88.7 | 88.9 | | |
| Statistics Mean | 81.7 | 84.75 | 86.01 | 87.42 | 88.8 | 90.25 | 91.60 | 92.8 |
| Standard Dev. | 0.31 | 0.65 | 0.51 | 0.52 | 0.67 | 0.66 | 0.45 | 0.44 |
| n | 8 | 8 | 8 | 8 | 8 | 8 | 7 | 7 |

Table 3. Tabulation of the temperatures of the most prominent melting components found within the 5S rRNA melting curve. Peak numbers are indicated along the top row. Mean and standard deviations are given for each peak. Peak number 5 showed the most variation and the first peak showed the least variation, with standard deviations of 0.67° C. and 0.31.° C., respectively. Component melting peaks 7 and 8 were not decipherable from run number eight. Samples were subjected to a 0.05° C./s temperature ramp ranging from 60–97° C. Final concentrations for rRNA, SYBR Green I and the magnesium buffer were 1.0 mM, 1:15,000 stock dilution, and 1.0 mM $Mg^{+2}$, respectively.

Natural 5S rRNA System Discussion

Preliminary results from the analysis of a 5S rRNA sample yielded a melting curve profile with 8 identifiable components or transitions. Specific components of the 5S rRNA conformation have not yet been empirically or theoretically linked to individual melting transitions, however possible explanations exist.

Extensive information on the sequences and secondary structure information of 5S rRNA segments, from a wide range of organisms, can be found in nucleic acid related journals and ribosomal on-line databases. The basic, three-domain, two-dimensional 5S structure consists of five double stranded regions, two hairpin loops and three internal loops (bulges)(Brownlee et al, *Nature* 215(102):735–736 (1967); De Rijk, 1992; Specht et al., 1997; Szymanski et al., 1997). The length of the nucleic acid segment varies from species to species but is generally 120 bases long (Specht et al., 1997; Szymanski et al., 1997). Several hypervariable regions exist within the segment as well as one fairly conserved region. In addition, non-Watson-Crick interactions are often present within the E-loop of the 5S rRNA structure (Browlee et al., 1967; Voet at al., "Nucleic Acid Structure", *In Fundamentals of Biochemistry,* 1st edition, John Wiley & Sons, Inc., New York, N.Y. (1999) pp. 742–743). Standard base numbering and hairpin or loop identification is based on an *E. coli.* standard (Specht et al., 1997; Szymanski et al., 1997). FIG. 15 illustrates the basic organization of an *E. coli* derived 5S rRNA segment including domain identification and loop lettering.

Figure 13:
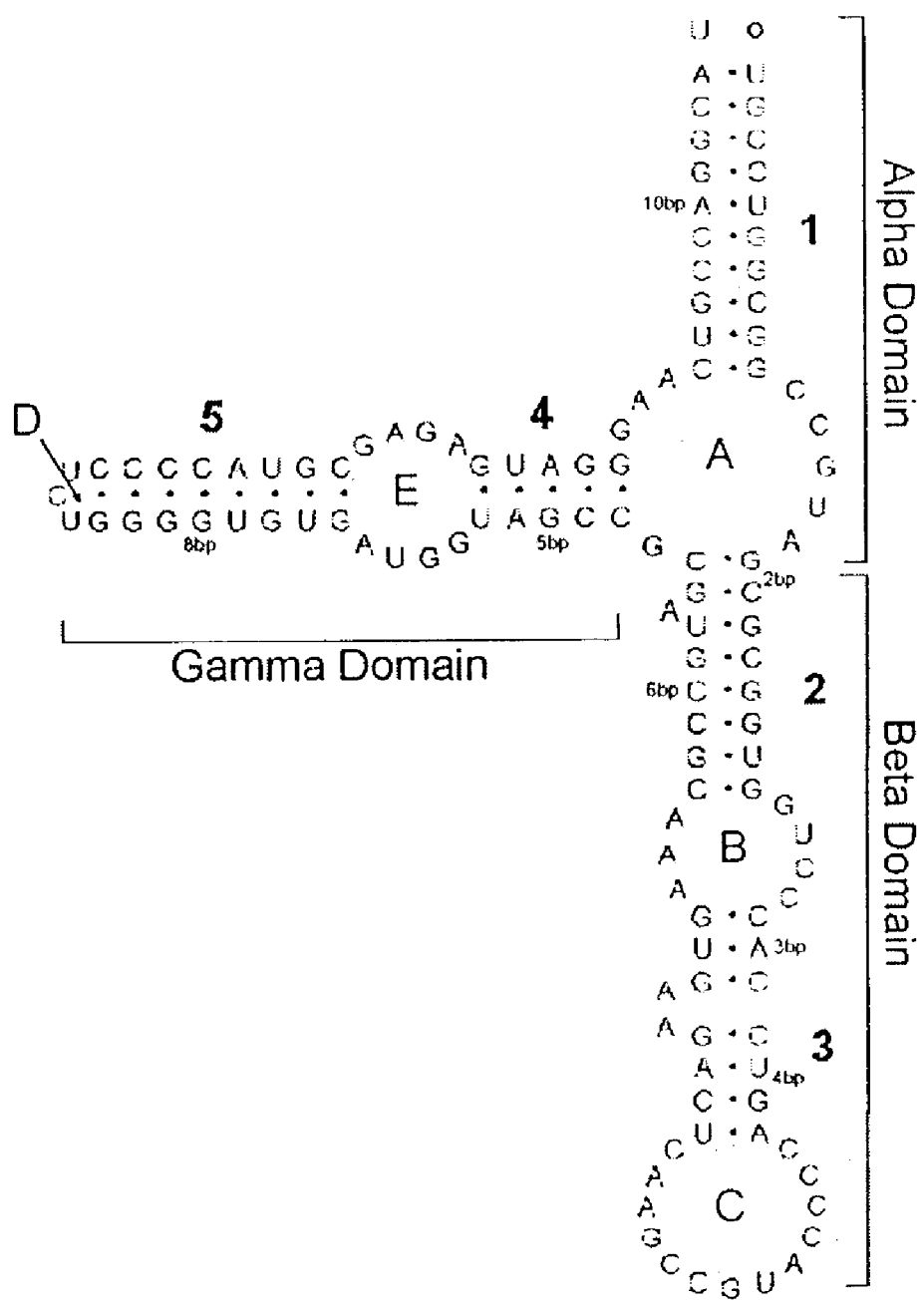
FIG. 13 is an illustration of the secondary structure from an *E. coli* 5S rRNA segment. Secondary structure of the segment is divided into the alpha, beta and gamma domains with specific loops or hairpins labeled with capital letters. Bolded numbers are used to identify specific double stranded segments. Smaller numbers identify the stem lengths of possible, author-identified, sub-domains. Seven of the eight observed components of the melting profile shown in FIG. 12 can possibly be accounted for by sub-dividing the 5S segment in this manner. The remaining melting transition might reflect melting of the non-Watson-Crick interactions that often occur within the internal E-loop.

A direct correlation between the secondary structure of the 5S rRNA molecule and the observed melting profile is not immediately evident. As illustrated in FIG. 13, usually only 5 double stranded segments are identified in the 5S sequence, yet there are 8 repeatable components of the melting profile. One could account for the additional three components in a number of ways. First, sample contamination is always a possibility. Since the exact isolation procedure was not disclosed and was performed by a second party, it can only be assumed that the sample is pure. Second, all melting components might not directly reflect double to single stranded transitions. The complete 5S conformation is three-dimensional and all structural transitions may not be strictly related to secondary structure. Acknowledging the presence of additional melting components that do not directly reflect double to single stranded transitions, furthermore, allows for insights into three-dimensional transitions as well. Third, two double stranded regions of the 5S rRNA molecule (segments labeled 2 and 3 in FIG. 13) can be subdivided into two parts, giving rise b seven total double stranded regions within the 5S molecule. Lastly, non-Watson-Crick interactions are often found within ribosomal secondary conformations (B rownlee et al., 1967; Voet et al., 1999). Several such nonstandard binding interactions have been identified in the E loop of the 5S molecule (Voet et al., 1999). If nonstandard interactions occur within regions that are thought to be loops, additional melting peaks representing loop formation would be observed.

Concerning the possibility of tertiary influences, as the three-dimensional structure begins to relax with the increase in temperature, it is reasonable to assume that the availability of SYBR Green I binding sites increases. The fluorescence of the dye would in turn increase slightly as more SYBR Green I binds to newly exposed double stranded DNA segments of the 5S molecule. The low –dF/dT "trough" evident in FIG. 12, which actually represents flattening of the melting curve, could then represent initial relaxation of the 5S tertiary structure. Techniques employed by Vamosi and Clegg (1998) that link specific properties of fluorophores, such as intensity, anisotropy, lifetime and spectra to different aspects of nucleic acid structure could be used to substantiate possible tertiary influences. In addition, applying the complex mathematical modeling performed by Doktycz et al., 1990, Santa Lucia, 1998, and Bonnet et al., *PNAS (USA)* 96:6171–6176 (1999), could also give insight into the specifics of the thermal melting of the 5S rRNA sequence.

Regardless of possible tertiary influences, the five double stranded segments should be observable, unless said tertiary influences overlap secondary structure transitions. Molecular Probes reports a major decrease in fluorescence intensity of SYBR Green I upon nucleic acid melting (Haugland, 1996) and since the LightCycler™ monitors fluorescence intensity, the major features of the melting profile are assumed to reflect secondary structure melting transitions within the 5S rRNA molecule. It was found from the model oligonucleotide system discussed earlier that the presence of more than one hairpin affects the $T_m$ value of the other hairpin. Using the same arguments used in the model oligonucleotide discussion the $T_m$ values of the five double stranded segments are more than likely shifted to higher temperatures. The longest model oligonucleotide (18 bp) melted at 77.8° C. The longest double stranded region in the 5S system is only 10 bp, yet major fluorescence changes are observed between 86° and 94° C. If any and all tertiary influences are assumed to occur before the most stable secondary transition, the peak labeled 8 in FIG. 12 would represent melting of the largest 5S hairpin stem. Peaks 7 to 4 would then represent stems melting from the seconded largest stem to the smallest.

As indicated in FIG. 13, both of the stems in the β-Domain contain mismatches. If these mismatches are made to distinguish sub-domains within the stems an additional interpretation of the 5S rRNA melting profile is indicated. Stem number 2 is then composed of a 2 bp stem and a 6 bp stem separated by one mismatch. Stem number 3 is divided into 3 bp and 4 bp stems separated by a 2-base insert. The number of possible separate melting domains now totals seven. The model oligonucleotide system demonstrated that the melting of a 3 bp stem can be monitored, and dividing the stems of the 5S rRNA systems into smaller subunits ranging in size from 2 bp to 8 bp is not unreasonable. All eight melting transitions can be accounted for if non-Watson-Crick interactions are considered within the E loop. If it is assumed the non-Watson-Crick interactions within the E loop are less stable than any of the other interactions, eight possible distinct melting domains exist. The possible interpretaton would then include the non-Watson-Crick interactions within the E loop, the 2 bp, 3 bp, 4 bp, 5 bp, 6 bp, 8 bp and the 10 bp stems, which could correspond to melting transitions at 81.6°, 84.8°, 86.8° C., 87.5° C., 88.9° C., 90.2°, 91.6° C. and 93.1° C., respectively. All eight possible transitions are accounted for in this manner but the affects of tertiary influences, though uncertain, are not considered.

Other explanations for the determined 5S rRNA $T_m$ profile are possible. As the melting of the 5S structure proceeds, loops of varying sizes are generated, which change the stability of the accompanying stems. The melting system is therefore very complex and may not proceed in the exact fashion outlined above. The division of stems into sub-stems, on the other hand is supported by observations gained by the model oligonucleotide system. The possible interpretation also assumes that all, conformational transitions occur between 80° and 95° C., which may not be the case. Results from the model oligonucleotide system do however support the possibility that duplexed regions within complex secondary organizations, as found in the 5S segment, will melt at high temperatures.

Even with the uncertainty concerning how the eight melting transitions relate to the 5S rRNA sample, the preliminary results are useful. With eight different components to consider, the possibility of observing a difference in melting profiles between several organisms would be expected. By comparing SYBR Green I derived results of natural secondary structures to other methods such as, hyperchromicity or differential scanning calorimetry (DSC), insights may be gained into the mechanics of the melting transitions. A complete thermodynamic study of 5S rRNA or rDNA sequences, using techniques and mathematical models used by Doktycz et al., 1990, Paner et al., 1990, and Vamosi and Clegg, 1998, could completely elucidate the melting transitions of the 5S segment. Specifics on the exact mechanisms behind the melting transitions however, do not need to be determined before the process may be used to distinguish organisms. As long as consistent differences are observed from one sample to the next, the analysis of secondary structure conformations by $T_m$ and SYBR Green I may be used to identify organisms.

The model system has proven to be a very powerful tool in showing the feasibility of detecting secondary structure characteristics within a molecule of nucleic acid. Natural occurring sequences are much more complex than the model system used in this study, as demonstrated in the 5S rRNA melting profile. Much work has been done in the sequencing and identification of secondary structures within ribosomal RNA. For example, 101 bulges or hairpin loops were identified in the 23s rRNA molecule obtained from *Pseudomonas cepacia* (Van Camp et al., 1993). In contrast, the 5S rRNA structure consists of only five double stranded regions, two hairpin loops and three internal loops (bulges) (De Rijk, 1992; Szymanski et al., 1997). In any case, the complexity of naturally-occurring secondary structures is tremendous. Within most of these sequences however, highly conserved regions exist which enable assays such as SSCP and ribotyping to differentiate samples at the organism level using PCR for segment amplification. Van Camp and colleagues identified several universal primer sites, which can be used to amplify hypervariable regions within the 23s gene (1993). Erik Avaniss-Aghajani et al. identified and tested a primer set "capable of amplifying the SSU [small subunit] rRNA from essentially all bacteria" for bacterial typing using ribotyping techniques (1994). Such regions are currently being used for assays such as SSCP and ribotyping and should also be good for secondary structure analysis using $T_m$ and SYBR Green I.

Much work has been done to identify universal primer sites that could be used to type a large number of bacterial specimens. Perhaps even better suited than 5S rRNA/rDNA for amplification of informative hypervariable regions containing secondary structure components might be the universal primers designed by several current researchers working with 16s and 23s rRNA genes (Anthony et al., 2000; Rantakokoo-Jalava et al., 2000; Widjojoatmodjo et al., 1994). Work performed by these research groups has found medically significant regions within the 16s and 23s genes that contain secondary structures within hypervariable segments. Specifically, the work done by Widjojoatmodjo demonstrates good species typing by SSCP with a small amplicon size, ranging from 108 bp to 300 bp (1994). Consistent yet differentiable melting profiles may be obtained from these same regions for analysis by the present invention.

The invention claimed is:

1. A method of characterizing a single stranded nucleic acid, said method comprising:
   a) combining a single stranded nucleic acid with a double stranded nucleic acid-specific dye to form a detectable complex between said dye and one or more double strand secondary structures within said single stranded nucleic acid; and
   b) varying the temperature of said single stranded nucleic acid at a rate of 0.01°–0.1° C./sec to determine the melting temperature ($T_m$) for each of said secondary structures in said detectable complex, wherein the $T_m$ is determined by measuring fluorescence emission of said double strand nucleic acid-specific dye while varying temperature of the nucleic acid, and wherein said melting temperature(s) define a $T_m$ profile characterizing said single stranded nucleic acid.

2. The method of claim 1, wherein said single stranded nucleic acid is an amplified nucleic acid product.

3. The method of claim 2, wherein said single stranded nucleic acid is a polymerase chain reaction (PCR) amplification product.

4. The method of claim 3, wherein said PCR is asymmetrical PCR.

5. The method of claim 2, wherein said single stranded nucleic acid is a product of an amplification reaction selected from the group consisting of strand displacement amplification (SDA), rolling circle amplification (RCA), nucleic acid sequence-based amplification (NASBA), transcription mediated amplification (TMA) and ligase chain reaction (LCR).

6. The method of claim 1, wherein said double stranded nucleic acid-specific dye is selected from the group consisting of SYBR® Green 1, SYBR® Gold, ethidium bromide, propidium bromide, Pico Green, Hoechst 33258, YO-PRO-1 and YO-YO-1.

7. The method of claim 6, wherein said double stranded nucleic acid-specific dye is SYBR® Green 1.

8. The method of claim 1, wherein said method further comprises: amplifying said single stranded nucleic acid prior to or concurrent with said determining of said $T_m$ profile.

9. The method of claim 1, wherein a change in fluorescence indicates a change in secondary structure of said single stranded nucleic acid.

10. A method of detecting a difference between the sequence of a first and a second single stranded nucleic acid, said method comprising:
    a) determining the $T_m$ profile of a first single stranded nucleic acid using a double stranded nucleic acid-specific dye by combining said first single stranded nucleic acid with said double stranded nucleic acid-specific dye to form a detectable complex between said dye and one or more double strand secondary structures within said first single stranded nucleic acid and measuring fluorescence emission of said double strand nucleic acid-specific dye while varying the temperature of said combination at a rate of 0.01°–0.1° C./sec; and
    b) comparing said $T_m$ profile of said first single stranded nucleic acid with the $T_m$ profile of said second single stranded nucleic acid; wherein a difference in $T_m$ profile between said first and said second single stranded nucleic acid indicates a difference in sequence between said first and second nucleic acids.

11. The method of claim 10, wherein said first single stranded nucleic acid is an amplified nucleic acid product.

12. The method of claim 10, wherein said method further comprises: amplifying said first single stranded nucleic acid prior to or concurrent with said determining of said $T_m$ profile.

13. The method of claim 10, wherein a change in fluorescence indicates a change in secondary structure of said single stranded nucleic acid.

14. The method of claim 10, wherein said double stranded nucleic acid-specific dye is selected from the group consisting of SYBR® Green I, SYBR® Gold, ethidium bromide, propidium bromide, Pico Green, Hoechst 33258, YO-PRO-1 and YO-YO-1.

15. A method of detecting an alteration in the sequence of a sample nucleic acid as compared with a nucleic acid having a known sequence, said method comprising, determining the $T_m$ profile of a single stranded nucleic acid sample using a double strand nucleic acid-specific dye by combining said single stranded nucleic acid sample with a double stranded nucleic acid-specific dye to form a detectable complex between said dye and one or more double strand secondary structures within said single stranded nucleic acid sample and measuring fluorescence emission of said double strand nucleic acid-specific dye while varying the temperature of said combination at a rate of 0.01°–0.1° C./sec, wherein a difference between the $T_m$ profile of said nucleic acid sample and the $T_m$ profile of said nucleic acid having a known sequence indicates an alteration in the sequence of said sample nucleic acid as compared to said known sequence.

16. The method of claim 15, wherein said single stranded nucleic acid sample is an amplified nucleic acid product.

17. The method of claim 16, wherein primer(s) used in said amplification is derived from the sequence of said nucleic acid having a known sequence.

18. The method of claim 15, wherein said method further comprises: amplifying said first single stranded nucleic acid prior to or concurrent with said determining of said $T_m$ profile.

19. The method of claim 18, wherein said amplification is performed using primer(s) derived from the sequence of said nucleic acid having a known sequence.

20. The method of claim 15, wherein said double stranded nucleic acid-specific dye is selected from the group consisting of SYBR® Green 1, SYBR® Gold, ethidium bromide, propidium bromide, Pico Green, Hoechst 33258, YO-PRO-1 and YO-YO-1.

21. A method of detecting a mutation in a nucleic acid as compared to a known nucleic acid, said method comprising: determining the $T_m$ profile of a single-stranded nucleic acid sample using a double strand nucleic acid-specific dye by combining said single stranded nucleic acid sample with said double stranded nucleic acid-specific dye to form a detectable complex between said dye and one or more double strand secondary structures within said single stranded nucleic acid sample and measuring fluorescence emission of said double strand nucleic acid-specific dye while varying the temperature of said combination at a rate of 0.01°–0.1° C./sec, wherein a difference between the $T_m$ profile of said nucleic acid sample and the wild-type nucleic acid indicates the presence of a mutation in said nucleic acid as compared to said wild-type nucleic acid.

22. The method of claim 21, wherein said single stranded nucleic acid sample is an amplified nucleic acid product.

23. The method of claim 22, wherein primer(s) used in said amplification are derived from the sequence of said known nucleic acid.

24. The method of claim 21, wherein said method further comprises: amplifying said first single stranded nucleic acid prior to or concurrent with said determining of said $T_m$ profile.

25. The method of claim 24, wherein said amplification is performed using primer(s) derived from the sequence of said known nucleic acid.

26. The method of claim 21, wherein said double stranded nucleic acid-specific dye is selected from the group consisting of SYBR® Green I, SYBR® Gold, ethidium bromide, propidium bromide, Pico Green, Hoechst 33258, YO-PRO-1 and YO-YO-1.

27. The method of claim 1, 10, or 15 wherein the temperature range of said $T_m$ profile is between about 20° C. and about 100° C.

28. The method of claim 27, wherein said lower limit of said temperature range is less than about 40° C.

29. The method of claim 28, wherein said lower limit of said temperature range is less than about 35° C.

30. The method of claim 21, wherein said known nucleic acid is a wild-type nucleic acid.

31. The method of claim 1, wherein the double strand nucleic acid-specific dye is a saturation dye.

32. A method of characterizing a single stranded nucleic acid, said method comprising:
a) combining a single stranded nucleic acid with a saturation dye to form a detectable complex between said dye and one or more double strand secondary structures within said single stranded nucleic acid; and
b) varying the temperature of said single stranded nucleic acid to determine the melting temperature ($T_m$) for each of said secondary structures in said detectable complex, wherein said melting temperature(s) define a $T_m$ profile characterizing said single stranded nucleic acid.

33. The method of claim 32, wherein said single stranded nucleic acid is an amplified nucleic acid product.

34. The method of claim 33, wherein said single stranded nucleic acid is a polymerase chain reaction (PCR) amplified product.

35. The method of claim 34, wherein said PCR is asymmetrical PCR.

36. The method of claim 34, wherein the dye is present during PCR.

37. The method of claim 32, wherein the dye has a percent saturation of at least 90%.

38. A method of detecting a mutation in a nucleic acid as compared to a known nucleic acid, said method comprising: determining the $T_m$ profile of a single-stranded nucleic acid sample using a saturation dye, wherein a difference between the $T_m$ profile of said nucleic acid sample and the wild-type nucleic acid indicates the presence of a mutation in said nucleic acid as compared to said wild-type nucleic acid.

39. The method of claim 38, wherein said single stranded nucleic acid sample is an amplified nucleic acid product.

40. The method of claim 39, wherein primer(s) used in said amplification are derived from the sequence of said known nucleic acid.

41. The method of claim 39, wherein the dye is present during amplification.

42. The method of claim 38, wherein said method further comprises: amplifying said first single stranded nucleic acid prior to or concurrent with said determining of said $T_m$ profile.

43. The method of claim 38, wherein the dye has a percent saturation of at least 90%.

* * * * *